United States Patent [19]
Low et al.

[11] Patent Number: 6,071,891
[45] Date of Patent: Jun. 6, 2000

[54] INSULIN-LIKE GROWTH FACTOR 1 RECEPTORS (IGF-1R) ANTISENSE OLIGONUCLEOTIDE CELLS COMPOSITION

[75] Inventors: Walter C. Low, Shorewood; Margaret A. Wallenfriedman, Edina; Lan Chiang, Plymouth, all of Minn.

[73] Assignee: Regents of the University of Minnesota, Minneapolis, Minn.

[21] Appl. No.: 08/755,558

[22] Filed: Nov. 22, 1996

[51] Int. Cl.$^7$ .......................... A61K 48/00; A61K 35/12; C12N 15/85; C07H 21/04
[52] U.S. Cl. ............................ 514/44; 424/277.1; 435/6; 435/320.1; 435/325; 435/353; 514/44; 536/23.1; 536/24.31; 536/24.5
[58] Field of Search .......................... 435/6, 91.1, 172.1, 435/440, 320.1, 353, 325; 536/23.1, 24.31, 24.5; 514/44; 424/274.1

[56] References Cited

U.S. PATENT DOCUMENTS 5,643,788  7/1997  Baserga et al. .......................... 435/325

OTHER PUBLICATIONS

Resnicoff et al., Rat Glioblastoma Cells Expressing an Antisense RNA to the Insulin–Like Growth Factor–1 (IGF–1) Receptor are Nontumorigenic and Induce Regression of Wild–Type Tumors, Cancer Res. 54, 2218–2222 (1994).

Burfeind et al., Antisense RNA to the Type I Insulin–Like Growth Factor Receptor Suppresses Tumor Growth and Prevents Invasion by Rat Prostate Cancer Cells in Vivo, PNAs 93, 7263–7268 (Jul. 1996).

Gilboa, Immunotherapy of Cancer with Genetically Modified Tumor Vaccines, Seminars in Oncology 23 (1) 101–107 (Feb. 1996).

Calabretta, et al., 1993, *Cancer Treatment Reviews*, 19:169–179, "Prospects for gene–directed therapy with antisense oligodeoxynucleotides".

Carter and Lemoine, 1993, *Br. J. Cancer*, 67:869–876, Antisense technology for cancer therapy: does it make sense?.

Hall, et al., 1996 (Feb.), *Neurosurgery*, 38:2:376–383, "Antisense Oligonucleotides for Central Nervous System Tumors".

Leonetti, et al., 1993, *Progress in Nucleic Acid Research*, pp. 143–166, "Cell Delivery and Mechanisms of Action of Antisense Oligonucleotides".

Resnicoff, et al., 1993, *Laboratory Investigation*, 69:6:756–760, "Insulin–like Growth Factor–1 and its Receptor Mediate the Autocrine Proliferation of Human Ovarian Carcinoma Cell Lines".

Resnicoff, et al., Apr. 15, 1994, *Cancer Research*, 54:2218–2222 "Rat Glioblastoma Cells Expressing an Antisense RNA to the Insulin–like Growth Factor–1 (IGF–1) Receptor Are Nontumorigenic and Induce Regression of Wild–Type Tumores".

Resnicoff, et al., Sep. 15, 1994, *Cancer Research*, 54:4848–4850, "Growth Inhibition of Human Melanoma Cells in Nude Mice by Antisense Strategies to the Type 1 Insulin–like Growth Factor Receptor".

Resnicoff, et al., Jun. 1, 1995, *Cancer Research*, 55:2463–2469, "The Insulin–like Growth Factor I Receptor Protects Tumor Cells from Apoptosis in Vivo".

Resnicoff, et al., Sep. 1, 1995, *Cancer Research*, 55:373903741, "Correlation between Apoptosis, Tumorigenesis, and Levels of Insulin–like Growth Factor I Receptors".

Resnicoff, et al., 1996, *Cancer Immunol Immunother*, 42:64–68, "Inhibition of rat C6 glioblastoma tumor growth by expression of insulin–like growth factor I receptor antisense mRNA".

Sell, et al., Jan. 15, 1995, *Cancer Research*, 55:303–306, "Insulin–like Growth Factor I (IGE–I) and the IGF–I Receptor Prevent Etoposide–induced Apoptosis".

Stein and Chang, Aug. 20, 1993, *Science* 261:1004–1011, "Antisense Oligonucleotides as Therapeutic Agents—Is the Bullet Really Magical?".

Trojan, et al., Jun. 1992, *Proc. Natl. Acad. Sci, USA*, 89:4874–4878, "Loss of tumorigenicity of rat glioblastoma directed by episome–based antisense cDNA transcription of insulin–like growth factor I".

Trojan, et al., Jan. 1, 1993, *Science*, 259:94–97, "Treatment and Prevention of Rat Glioblastoma by Immunogenic C6 Cells Expressing Antisense Insulin–Like Growth Factor I RNA".

Trojan, et al., Jun. 1994, *Proc. Natl. Acad. Sci. USA*, 91:6088–6092, "Gene therapy of murine teratocarcinoma: Separate functions for insulin–like growth factors I and II in immunogenicity and differentiation".

Wallenfriedman, et al., 1996, Abstract—AACR—Effects of IGF–1R antisense and nonsense oligonucleotide administration on 9L glioblastoma and MAT B3 breast tumor growth in Fischer 344 rats.

Baserga, R., "Controlling IGF–receptor function: a possible strategy for tumor therapy", TIBTECH, 14: 150–152 (May 1996).

Wallenfriedman, M.A. et al., "IGF–1 R Antisense and Nonsense Oligonucleotide Therapy for 9L Glioblastoma Results in an Immune Response Against an Unrelated Syngeneic Tumor in Fischer 344 Rats", *Society for Neuroscience*, 22: 1 page (1966).

"Experimental Therapeutics", *Proceedings of the American Association for Cancer Research*, 37: Cover and p. 354 (Mar. 1996).

"Immunology/Preclinical and Clinical Biological Therapy", *Proceedings of the American Association for Cancer Research*, 38: Cover and p. 617 (Mar. 1997).

*Primary Examiner*—John S. Brusca
*Assistant Examiner*—Mark L. Shibuya
*Attorney, Agent, or Firm*—Merchant & Gould P.C.

[57] ABSTRACT

A composition and method for inhibiting the growth and metastasis of breast tumors, including a tumor immunogen derived from breast tumor cells treated with an antisense oligonucleotide complementary to a gene or mRNA for the receptor for insulin-like growth factor type 1.

17 Claims, 14 Drawing Sheets

FIG. 6A

| | | | | | | | | | | | | | | | | |
|---|---|---|---|---|---|---|---|---|---|---|---|---|---|---|---|---|
| TTTTTTTTTT | TTTTGAGAAA | GGGAATTTCA | TCCCAAATAA | AAGGA | ATG | AAG | TCT | GGC | | | | | | | | 57 |
| | | | | | Met | Lys | Ser | Gly | | | | | | | | |
| | | | | | 1 | | | | | | | | | | | |

```
TCC GGA GGA GGG TCC CCG ACC TCG CTG TGG GGG CTC CTG TTT CTC TCC    105
Ser Gly Gly Gly Ser Pro Thr Ser Leu Trp Gly Leu Leu Phe Leu Ser
 5              10              15              20

GCC GCG CTC TCG CTC TGG CCG ACG AGT GGA GAA ATC TGC GGG CCA GGC    153
Ala Ala Leu Ser Leu Trp Pro Thr Ser Gly Glu Ile Cys Gly Pro Gly
            25              30              35

ATC GAC ATC CGC AAC GAC TAT CAG CAG CTG AAG CGC CTG GAG AAC TGC    201
Ile Asp Ile Arg Asn Asp Tyr Gln Gln Leu Lys Arg Leu Glu Asn Cys
         40              45              50

ACG GTG ATC GAG GGC TAC CTC CAC ATC CTG CTC ATC TCC AAG GCC GAG    249
Thr Val Ile Glu Gly Tyr Leu His Ile Leu Leu Ile Ser Lys Ala Glu
         55              60              65

GAC TAC CGC AGC TAC CGC TTC CCC AAG CTC ACG GTC ATT ACC GAG TAC    297
Asp Tyr Arg Ser Tyr Arg Phe Pro Lys Leu Thr Val Ile Thr Glu Tyr
     70              75              80

TTG CTG CTG TTC CGA GTG GCT GGC CTC GAG AGC CTC GGA GAC CTC TTC    345
Leu Leu Leu Phe Arg Val Ala Gly Leu Glu Ser Leu Gly Asp Leu Phe
 85              90              95             100

CCC AAC CTC ACG GTC ATC CGC GGC TGG AAA CTC TTC TAC AAC TAC GCC    393
Pro Asn Leu Thr Val Ile Arg Gly Trp Lys Leu Phe Tyr Asn Tyr Ala
            105             110             115

CTG GTC ATC TTC GAG ATG ACC AAT CTC AAG GAT ATT GGG CTT TAC AAC    441
Leu Val Ile Phe Glu Met Thr Asn Leu Lys Asp Ile Gly Leu Tyr Asn
            120             125             130

CTG AGG AAC ATT ACT CGG GGG GCC ATC AGG ATT GAG AAA AAT GCT GAC    489
Leu Arg Asn Ile Thr Arg Gly Ala Ile Arg Ile Glu Lys Asn Ala Asp
            135             140             145

CTC TGT TAC CTC TCC ACT GTG GAC TGG TCC CTG ATC CTG GAT GCG GTG    537
Leu Cys Tyr Leu Ser Thr Val Asp Trp Ser Leu Ile Leu Asp Ala Val
        150             155             160
```

FIG. 6B

```
TCC AAT AAC TAC ATT GTG GGG AAT AAG CCC CCA AAG GAA TGT GGG GAC      585
Ser Asn Asn Tyr Ile Val Gly Asn Lys Pro Pro Lys Glu Cys Gly Asp
165             170             175             180

CTG TGT CCA GGG ACC ATG GAG GAG AAG CCG ATG TGT GAG AAG ACC ACC      633
Leu Cys Pro Gly Thr Met Glu Glu Lys Pro Met Cys Glu Lys Thr Thr
                185             190             195

ATC AAC AAT GAG TAC AAC TAC CGC TGC TGG ACC ACA AAC CGC TGC CAG      681
Ile Asn Asn Glu Tyr Asn Tyr Arg Cys Trp Thr Thr Asn Arg Cys Gln
            200             205             210

AAA ATG TGC CCA AGC ACG TGT GGG AAG CGG GCG TGC ACC GAG AAC AAT      729
Lys Met Cys Pro Ser Thr Cys Gly Lys Arg Ala Cys Thr Glu Asn Asn
        215             220             225

GAG TGC TGC CAC CCC GAG TGC CTG GGC AGC TGC AGC GCG CCT GAC AAC      777
Glu Cys Cys His Pro Glu Cys Leu Gly Ser Cys Ser Ala Pro Asp Asn
    230             235             240

GAC ACG GCC TGT GTA GCT TGC CGC CAC TAC TAC TAT GCC GGT GTC TGT      825
Asp Thr Ala Cys Val Ala Cys Arg His Tyr Tyr Tyr Ala Gly Val Cys
245             250             255             260

GTG CCT GCC TGC CCG CCC AAC ACC TAC AGG TTT GAG GGC TGG CGC TGT      873
Val Pro Ala Cys Pro Pro Asn Thr Tyr Arg Phe Glu Gly Trp Arg Cys
                265             270             275

GTG GAC CGT GAC TTC TGC GCC AAC ATC CTC AGC GCC GAG AGC AGC GAC      921
Val Asp Arg Asp Phe Cys Ala Asn Ile Leu Ser Ala Glu Ser Ser Asp
                280             285             290

TCC GAG GGG TTT GTG ATC CAC GAC GGC GAG TGC ATG CAG GAG TGC CCC      969
Ser Glu Gly Phe Val Ile His Asp Gly Glu Cys Met Gln Glu Cys Pro
            295             300             305

TCG GGC TTC ATC CGC AAC GGC AGC CAG AGC ATG TAC TGC ATC CCT TGT     1017
Ser Gly Phe Ile Arg Asn Gly Ser Gln Ser Met Tyr Cys Ile Pro Cys
        310             315             320

GAA GGT CCT TGC CCG AAG GTC TGT GAG GAA GAA AAG AAA ACA AAG ACC     1065
Glu Gly Pro Cys Pro Lys Val Cys Glu Glu Glu Lys Lys Thr Lys Thr
325             330             335             340
```

FIG. 6C

| | |
|---|---|
| ATT GAT TCT GTT ACT TCT GCT CAG ATG CTC CAA GGA TGC ACC ATC TTC<br>Ile Asp Ser Val Thr Ser Ala Gln Met Leu Gln Gly Cys Thr Ile Phe<br>                345                      350                  355 | 1113 |
| AAG GGC AAT TTG CTC ATT AAC ATC CGA CGG GGG AAT AAC ATT GCT TCA<br>Lys Gly Asn Leu Leu Ile Asn Ile Arg Arg Gly Asn Asn Ile Ala Ser<br>                360                      365                  370 | 1161 |
| GAG CTG GAG AAC TTC ATG GGG CTC ATC GAG GTG GTG ACG GGC TAC GTG<br>Glu Leu Glu Asn Phe Met Gly Leu Ile Glu Val Val Thr Gly Tyr Val<br>                375                      380                  385 | 1209 |
| AAG ATC CGC CAT TCT CAT GCC TTG GTC TCC TTG TCC TTC CTA AAA AAC<br>Lys Ile Arg His Ser His Ala Leu Val Ser Leu Ser Phe Leu Lys Asn<br>        390                      395                  400 | 1257 |
| CTT CGC CTC ATC CTA GGA GAG GAG CAG CTA GAA GGG AAT TAC TCC TTC<br>Leu Arg Leu Ile Leu Gly Glu Glu Gln Leu Glu Gly Asn Tyr Ser Phe<br>405                      410                      415                  420 | 1305 |
| TAC GTC CTC GAC AAC CAG AAC TTG CAG CAA CTG TGG GAC TGG GAC CAC<br>Tyr Val Leu Asp Asn Gln Asn Leu Gln Gln Leu Trp Asp Trp Asp His<br>                425                      430                  435 | 1353 |
| CGC AAC CTG ACC ATC AAA GCA GGG AAA ATG TAC TTT GCT TTC AAT CCC<br>Arg Asn Leu Thr Ile Lys Ala Gly Lys Met Tyr Phe Ala Phe Asn Pro<br>                440                      445                  450 | 1401 |
| AAA TTA TGT GTT TCC GAA ATT TAC CGC ATG GAG GAA GTG ACG GGG ACT<br>Lys Leu Cys Val Ser Glu Ile Tyr Arg Met Glu Glu Val Thr Gly Thr<br>        455                      460                  465 | 1449 |
| AAA GGG CGC CAA AGC AAA GGG GAC ATA AAC ACC AGG AAC AAC GGG GAG<br>Lys Gly Arg Gln Ser Lys Gly Asp Ile Asn Thr Arg Asn Asn Gly Glu<br>                470                      475                  480 | 1497 |
| AGA GCC TCC TGT GAA AGT GAC GTC CTG CAT TTC ACC TCC ACC ACC ACG<br>Arg Ala Ser Cys Glu Ser Asp Val Leu His Phe Thr Ser Thr Thr Thr<br>485                      490                      495                  500 | 1545 |
| TCG AAG AAT CGC ATC ATC ATA ACC TGG CAC CGG TAC CGG CCC CCT GAC<br>Ser Lys Asn Arg Ile Ile Ile Thr Trp His Arg Tyr Arg Pro Pro Asp<br>                505                      510                  515 | 1593 |

FIG. 6D

| | | | | | | | | | | | | | | | |
|---|---|---|---|---|---|---|---|---|---|---|---|---|---|---|---|
| TAC | AGG | GAT | CTC | ATC | AGC | TTC | ACC | GTT | TAC | TAC | AAG | GAA | GCA | CCC | TTT | 1641
| Tyr | Arg | Asp | Leu | Ile | Ser | Phe | Thr | Val | Tyr | Tyr | Lys | Glu | Ala | Pro | Phe |
| | | | 520 | | | | 525 | | | | | 530 | | | |

AAG AAT GTC ACA GAG TAT GAT GGG CAG GAT GCC TGC GGC TCC AAC AGC   1689
Lys Asn Val Thr Glu Tyr Asp Gly Gln Asp Ala Cys Gly Ser Asn Ser
            535             540             545

TGG AAC ATG GTG GAC GTG GAC CTC CCG CCC AAC AAG GAC GTG GAG CCC   1737
Trp Asn Met Val Asp Val Asp Leu Pro Pro Asn Lys Asp Val Glu Pro
550             555             560

GGC ATC TTA CTA CAT GGG CTG AAG CCC TGG ACT CAG TAC GCC GTT TAC   1785
Gly Ile Leu Leu His Gly Leu Lys Pro Trp Thr Gln Tyr Ala Val Tyr
565             570             575             580

GTC AAG GCT GTG ACC CTC ACC ATG GTG GAG AAC GAC CAT ATC CGT GGG   1833
Val Lys Ala Val Thr Leu Thr Met Val Glu Asn Asp His Ile Arg Gly
            585             590             595

GCC AAG AGT GAG ATC TTG TAC ATT CGC ACC AAT GCT TCA GTT CCT TCC   1881
Ala Lys Ser Glu Ile Leu Tyr Ile Arg Thr Asn Ala Ser Val Pro Ser
            600             605             610

ATT CCC TTG GAC GTT CTT TCA GCA TCG AAC TCC TCT TCT CAG TTA ATC   1929
Ile Pro Leu Asp Val Leu Ser Ala Ser Asn Ser Ser Ser Gln Leu Ile
            615             620             625

GTG AAG TGG AAC CCT CCC TCT CTG CCC AAC GGC AAC CTG AGT TAC TAC   1977
Val Lys Trp Asn Pro Pro Ser Leu Pro Asn Gly Asn Leu Ser Tyr Tyr
            630             635             640

ATT GTG CGC TGG CAG CGG CAG CCT CAG GAC GGC TAC CTT TAC CGG CAC   2025
Ile Val Arg Trp Gln Arg Gln Pro Gln Asp Gly Tyr Leu Tyr Arg His
645             650             655             660

AAT TAC TGC TCC AAA GAC AAA ATC CCC ATC AGG AAG TAT GCC GAC GGC   2073
Asn Tyr Cys Ser Lys Asp Lys Ile Pro Ile Arg Lys Tyr Ala Asp Gly
            665             670             675

ACC ATC GAC ATT GAG GAG GTC ACA GAG AAC CCC AAG ACT GAG GTG TGT   2121
Thr Ile Asp Ile Glu Glu Val Thr Glu Asn Pro Lys Thr Glu Val Cys
            680             685             690

FIG. 6E

```
GGT GGG GAG AAA GGG CCT TGC TGC GCC TGC CCC AAA ACT GAA GCC GAG      2169
Gly Gly Glu Lys Gly Pro Cys Cys Ala Cys Pro Lys Thr Glu Ala Glu
        695             700             705

AAG CAG GCC GAG AAG GAG GAG GCT GAA TAC CGC AAA GTC TTT GAG AAT      2217
Lys Gln Ala Glu Lys Glu Glu Ala Glu Tyr Arg Lys Val Phe Glu Asn
    710             715             720

TTC CTG CAC AAC TCC ATC TTC GTG CCC AGA CCT GAA AGG AAG CGG AGA      2265
Phe Leu His Asn Ser Ile Phe Val Pro Arg Pro Glu Arg Lys Arg Arg
725             730             735             740

GAT GTC ATG CAA GTG GCC AAC ACC ACC ATG TCC AGC CGA AGC AGG AAC      2313
Asp Val Met Gln Val Ala Asn Thr Thr Met Ser Ser Arg Ser Arg Asn
            745             750             755

ACC ACG GCC GCA GAC ACC TAC AAC ATC ACC GAC CCG GAA GAG CTG GAG      2361
Thr Thr Ala Ala Asp Thr Tyr Asn Ile Thr Asp Pro Glu Glu Leu Glu
        760             765             770

ACA GAG TAC CCT TTC TTT GAG AGC AGA GTG GAT AAC ACG GAG AGA ACT      2409
Thr Glu Tyr Pro Phe Phe Glu Ser Arg Val Asp Asn Thr Glu Arg Thr
        775             780             785

GTC ATT TCT AAC CTT CGG CCT TTC ACA TTG TAC CGC ATC GAT ATC CAC      2457
Val Ile Ser Asn Leu Arg Pro Phe Thr Leu Tyr Arg Ile Asp Ile His
        790             795             800

AGC TGC AAC CAC GAG GCT GAG AAG CTG GGC TGC AGC GCC TCC AAC TTC      2505
Ser Cys Asn His Glu Ala Glu Lys Leu Gly Cys Ser Ala Ser Asn Phe
805             810             815             820

GTC TTT GCA AGG ACT ATG CCC GCA GAA GGA GCA GAT GAC ATT CCT GGG      2553
Val Phe Ala Arg Thr Met Pro Ala Glu Gly Ala Asp Asp Ile Pro Gly
            825             830             835

CCA GTG ACC TGG GAG CCA AGG CCT GAA AAC TCC ATC TTT TTA AAG TGG      2601
Pro Val Thr Trp Glu Pro Arg Pro Glu Asn Ser Ile Phe Leu Lys Trp
            840             845             850

CCG GAA CCT GAG AAT CCC AAT GGA TTG ATT CTA ATG TAT GAA ATA AAA      2649
Pro Glu Pro Glu Asn Pro Asn Gly Leu Ile Leu Met Tyr Glu Ile Lys
        855             860             865
```

FIG. 6F

| | |
|---|---|
| TAC GGA TCA CAA GTT GAG GAT CAG CGA GAA TGT GTG TCC AGA CAG GAA<br>Tyr Gly Ser Gln Val Glu Asp Gln Arg Glu Cys Val Ser Arg Gln Glu<br>    870                            875                        880 | 2697 |
| TAC AGG AAG TAT GGA GGG GCC AAG CTA AAC CGG CTA AAC CCG GGG AAC<br>Tyr Arg Lys Tyr Gly Gly Ala Lys Leu Asn Arg Leu Asn Pro Gly Asn<br>885                        890                        895                      900 | 2745 |
| TAC ACA GCC CGG ATT CAG GCC ACA TCT CTC TCT GGG AAT GGG TCG TGG<br>Tyr Thr Ala Arg Ile Gln Ala Thr Ser Leu Ser Gly Asn Gly Ser Trp<br>                 905                      910                      915 | 2793 |
| ACA GAT CCT GTG TTC TTC TAT GTC CAG GCC AAA ACA GGA TAT GAA AAC<br>Thr Asp Pro Val Phe Phe Tyr Val Gln Ala Lys Thr Gly Tyr Glu Asn<br>           920                      925                      930 | 2841 |
| TTC ATC CAT CTG ATC ATC GCT CTG CCC GTC GCT GTC CTG TTG ATC GTG<br>Phe Ile His Leu Ile Ile Ala Leu Pro Val Ala Val Leu Leu Ile Val<br>          935                      940                      945 | 2889 |
| GGA GGG TTG GTG ATT ATG CTG TAC GTC TTC CAT AGA AAG AGA AAT AAC<br>Gly Gly Leu Val Ile Met Leu Tyr Val Phe His Arg Lys Arg Asn Asn<br>    950                            955                      960 | 2937 |
| AGC AGG CTG GGG AAT GGA GTG CTG TAT GCC TCT GTG AAC CCG GAG TAC<br>Ser Arg Leu Gly Asn Gly Val Leu Tyr Ala Ser Val Asn Pro Glu Tyr<br>965                        970                        975                      980 | 2985 |
| TTC AGC GCT GCT GAT GTG TAC GTT CCT GAT GAG TGG GAG GTG GCT CGG<br>Phe Ser Ala Ala Asp Val Tyr Val Pro Asp Glu Trp Glu Val Ala Arg<br>                 985                      990                      995 | 3033 |
| GAG AAG ATC ACC ATG AGC CGG GAA CTT GGG CAG GGG TCG TTT GGG ATG<br>Glu Lys Ile Thr Met Ser Arg Glu Leu Gly Gln Gly Ser Phe Gly Met<br>            1000                      1005                    1010 | 3081 |
| GTC TAT GAA GGA GTT GCC AAG GGT GTG GTG AAA GAT GAA CCT GAA ACC<br>Val Tyr Glu Gly Val Ala Lys Gly Val Val Lys Asp Glu Pro Glu Thr<br>        1015                      1020                    1025 | 3129 |
| AGA GTG GCC ATT AAA ACA GTG AAC GAG GCC GCA AGC ATG CGT GAG AGG<br>Arg Val Ala Ile Lys Thr Val Asn Glu Ala Ala Ser Met Arg Glu Arg<br>    1030                      1035                    1040 | 3177 |

FIG. 6G

| | |
|---|---|
| ATT GAG TTT CTC AAC GAA GCT TCT GTG ATG AAG GAG TTC AAT TGT CAC<br>Ile Glu Phe Leu Asn Glu Ala Ser Val Met Lys Glu Phe Asn Cys His<br>1045                    1050                   1055                 1060 | 3225 |
| CAT GTG GTG CGA TTG CTG GGT GTG GTG TCC CAA GGC CAG CCA ACA CTG<br>His Val Val Arg Leu Leu Gly Val Val Ser Gln Gly Gln Pro Thr Leu<br>                1065                   1070                 1075 | 3273 |
| GTC ATC ATG GAA CTG ATG ACA CGG GGC GAT CTC AAA AGT TAT CTC CGG<br>Val Ile Met Glu Leu Met Thr Arg Gly Asp Leu Lys Ser Tyr Leu Arg<br>            1080                   1085                 1090 | 3321 |
| TCT CTG AGG CCA GAA ATG GAG AAT AAT CCA GTC CTA GCA CCT CCA AGC<br>Ser Leu Arg Pro Glu Met Glu Asn Asn Pro Val Leu Ala Pro Pro Ser<br>         1095                   1100                 1105 | 3369 |
| CTG AGC AAG ATG ATT CAG ATG GCC GGA GAG ATT GCA GAC GGC ATG GCA<br>Leu Ser Lys Met Ile Gln Met Ala Gly Glu Ile Ala Asp Gly Met Ala<br>      1110                   1115                 1120 | 3417 |
| TAC CTC AAC GCC AAT AAG TTC GTC CAC AGA GAC CTT GCT GCC CGG AAT<br>Tyr Leu Asn Ala Asn Lys Phe Val His Arg Asp Leu Ala Ala Arg Asn<br>1125                    1130                   1135                 1140 | 3465 |
| TGC ATG GTA GCC GAA GAT TTC ACA GTC AAA ATC GGA GAT TTT GGT ATG<br>Cys Met Val Ala Glu Asp Phe Thr Val Lys Ile Gly Asp Phe Gly Met<br>              1145                   1150                 1155 | 3513 |
| ACG CGA GAT ATC TAT GAG ACA GAC TAT TAC CGG AAA GGA GGC AAA GGG<br>Thr Arg Asp Ile Tyr Glu Thr Asp Tyr Tyr Arg Lys Gly Gly Lys Gly<br>            1160                   1165                 1170 | 3561 |
| CTG CTG CCC GTG CGC TGG ATG TCT CCT GAG TCC CTC AAG GAT GGA GTC<br>Leu Leu Pro Val Arg Trp Met Ser Pro Glu Ser Leu Lys Asp Gly Val<br>        1175                   1180                 1185 | 3609 |
| TTC ACC ACT TAC TCG GAC GTC TGG TCC TTC GGG GTC GTC CTC TGG GAG<br>Phe Thr Thr Tyr Ser Asp Val Trp Ser Phe Gly Val Val Leu Trp Glu<br>     1190                   1195                 1200 | 3657 |
| ATC GCC ACA CTG GCC GAG CAG CCC TAC CAG GGC TTG TCC AAC GAG CAA<br>Ile Ala Thr Leu Ala Glu Gln Pro Tyr Gln Gly Leu Ser Asn Glu Gln<br>1205                    1210                   1215                 1220 | 3705 |

FIG. 6H

| | |
|---|---:|
| GTC CTT CGC TTC GTC ATG GAG GGC GGC CTT CTG GAC AAG CCA GAC AAC<br>Val Leu Arg Phe Val Met Glu Gly Gly Leu Leu Asp Lys Pro Asp Asn<br>              1225                  1230                      1235 | 3753 |
| TGT CCT GAC ATG CTG TTT GAA CTG ATG CGC ATG TGC TGG CAG TAT AAC<br>Cys Pro Asp Met Leu Phe Glu Leu Met Arg Met Cys Trp Gln Tyr Asn<br>              1240                  1245                      1250 | 3801 |
| CCC AAG ATG AGG CCT TCC TTC CTG GAG ATC ATC AGC AGC ATC AAA GAG<br>Pro Lys Met Arg Pro Ser Phe Leu Glu Ile Ile Ser Ser Ile Lys Glu<br>              1255                  1260                      1265 | 3849 |
| GAG ATG GAG CCT GGC TTC CGG GAG GTC TCC TTC TAC TAC AGC GAG GAG<br>Glu Met Glu Pro Gly Phe Arg Glu Val Ser Phe Tyr Tyr Ser Glu Glu<br>    1270                  1275                      1280 | 3897 |
| AAC AAG CTG CCC GAG CCG GAG GAG CTG GAC CTG GAG CCA GAG AAC ATG<br>Asn Lys Leu Pro Glu Pro Glu Glu Leu Asp Leu Glu Pro Glu Asn Met<br>1285                  1290                  1295                  1300 | 3945 |
| GAG AGC GTC CCC CTG GAC CCC TCG GCC TCC TCG TCC TCC CTG CCA CTG<br>Glu Ser Val Pro Leu Asp Pro Ser Ala Ser Ser Ser Ser Leu Pro Leu<br>              1305                  1310                      1315 | 3993 |
| CCC GAC AGA CAC TCA GGA CAC AAG GCC GAG AAC GGC CCC GGC CCT GGG<br>Pro Asp Arg His Ser Gly His Lys Ala Glu Asn Gly Pro Gly Pro Gly<br>              1320                  1325                      1330 | 4041 |
| GTG CTG GTC CTC CGC GCC AGC TTC GAC GAG AGA CAG CCT TAC GCC CAC<br>Val Leu Val Leu Arg Ala Ser Phe Asp Glu Arg Gln Pro Tyr Ala His<br>              1335                  1340                      1345 | 4089 |
| ATG AAC GGG GGC CGC AAG AAC GAG CGG GCC TTG CCG CTG CCC CAG TCT<br>Met Asn Gly Gly Arg Lys Asn Glu Arg Ala Leu Pro Leu Pro Gln Ser<br>              1350                  1355                      1360 | 4137 |
| TCG ACC TGC TGA TCCTTGGATC CTGAATCTGT GCAAACAGTA ACGTGTGCGC ACGCGC<br>Ser Thr Cys<br>1365 | 4195 |
| AGCGGGGTGG GGGGGGAGAG AGAGTTTTAA CAATCCATTC ACAAGCCTCC TGTACCTCAG | 4255 |
| TGGATCTTCA GTTCTGCCCT TGCTGCCCGC GGGAGACAGC TTCTCTGCAG TAAAACACAT | 4315 |
| TTGGGATGTT CCTTTTTTCA ATATGCAAGC AGCTTTTTAT TCCCTGCCCA AACCCTTAAC | 4375 |
| TGACATGGGC CTTTAAGAAC CTTAATGACA ACACTTAATA GCAACAGAGC ACTTGAGAAC | 4435 |
| CAGTCTCCTC ACTCTGTCCC TGTCCTTCCC TGTTCTCCCT TTCTCTCTCC TCTCTGCTTC | 4495 |
| ATAACGGAAA AATAATTGCC ACAAGTCCAG CTGGGAAGCC CTTTTTATCA GTTTGAGGAA | 4555 |

FIG. 6I

```
GTGGCTGTCC CTGTGGCCCC ATCCAACCAC TGTACACACC CGCCTGACAC CGTGGGTCAT  4615
TACAAAAAAA CACGTGGAGA TGGAAATTTT TACCTTTATC TTTCACCTTT CTAGGGACAT  4675
GAAATTTACA AAGGGCCATC GTTCATCCAA GGCTGTTACC ATTTTAACGC TGCCTAATTT  4735
TGCCAAAATC CTGAACTTTC TCCCTCATCG GCCCGGCGCT GATTCCTCGT GTCCGGAGGC  4795
ATGGGTGAGC ATGGCAGCTG GTTGCTCCAT TTGAGAGACA CGCTGGCGAC ACACTCCGTC  4855
CATCCGACTG CCCCTGCTGT GCTGCTCAGG GCCACAGGCA CACAGGTCTC ATTGCTTCTG  4915
ACTAGATTAT TATTTGGGGG AACTGGACAC AATAGGTCTT TCTCTCAGTG AAGGTGGGGA  4975
GAAGCTGAAC CGGC                                                    4989
```

INSULIN-LIKE GROWTH FACTOR 1 RECEPTORS (IGF-1R) ANTISENSE OLIGONUCLEOTIDE CELLS COMPOSITION

FIELD OF THE INVENTION

This invention relates to a vaccine and to a therapeutic method effective for inhibiting the growth of breast tumors and inhibiting local or metastatic breast tumor reoccurrence. Specifically, the invention demonstrates that peripheral administration of breast tumor immunogens derived from breast tumor cells treated with an antisense oligonucleotide complementary to the gene or mRNA for IGF-1 receptor effectively inhibits the growth of breast tumor cells and prevents metastasis of tumor cells, e.g., to the brain.

BACKGROUND OF THE INVENTION

Breast cancer is the most common malignancy in females in North America, becoming clinically apparent in one out of nine women. The prevalence of breast cancer is high compared to its annual incidence in other countries (estimated at greater than four times that in the UK). Thus, a therapy for this disease would provide a significant benefit to a large number of individual patients as well as a relief of health care resources.

Current treatment for breast cancer is directed at non-specific elimination-resection, administration of agents toxic to growing cells, or inhibition of receptor ligands required for cell growth. Examples include radiation, cytotoxic chemotherapy (e.g., doxorubicin, cyclophosphamide, methotrexate, 5-fluorouracil, mitomycin C and mitoxantrone) or hormonal manipulation to delete (e.g., ovarian ablation) or antagonize (e.g., tamoxifen, aromatase inhibitors) estrogen/progesterone stimulation of tumor growth. Because of their lack of tumor specificity, these therapies are poorly tolerated and become ineffective when the disease is widely metastatic.

These therapies have additional limitations. High doses of cytotoxic agents needed for therapeutic efficacy also destroy normal dividing immunological cells and gastrointestinal cells. Thus, administration of cytotoxic agents is limited by neutropenia, thrombocytopenia and malnutrition. Radiation and surgical therapies are limited to relatively-localized disease. All strategies are limited by the degree of deformity and/or disability that patients are willing to tolerate for only a modest increase in survival. Thus, there is need for a therapy which specifically targets a patient's malignancy and does not reduce the quality of the patient's remaining life.

Breast cancers are difficult targets because they are heterogeneous in a variety of features, including, for example, presence and absence of estrogen and progesterone receptors, and presence and absence of amplified growth factor receptors. In addition, the tumor cells may have a variety of different mutations in somatic proto-oncogenes, such as c-erb2, c-myc, int2, hst1, bcl1, and PRAD1, or tumor suppresser genes, including RB and TP53. Further, a patient may have more then one malignant cell type in the same tumor.

A population of diversified targets however, is exactly what a host's immune system is designed to screen and selectively eliminate. Vaccine-based immunotherapy has been shown to be effective in treating animal models of other types of cancers. The diversity of targets in breast cancer plus effectiveness in other types of cancer suggests that development of a vaccine-based immunotherapy might be effective for the treatment of breast cancer.

Antisense Oligonucleotides

Antisense oligonucleotides are nucleotide sequences that are complementary to specified segments of a targeted gene or mRNA. The binding of an antisense oligonucleotide to DNA or RNA within a cell can inhibit translation or transcription in the cell, which can disrupt gene expression. Typically, antisense oligonucleotides are about 14 to about 25 nucleotides in length, since it is believed that at least about 14 bases are required to specifically target a unique mammalian gene sequence. The sequence of an antisense oligonucleotide is chosen to provide specificity for a particular mammalian gene or mRNA sequence.

Antisense oligonucleotides can be synthesized with either natural or synthetic bases and with a natural phosphate or modified phosphate or sugar backbone. For example, phosphothioate, phosphonate, and other backbone modifications can significantly alter the biological half-life, and bioavailability of antisense oligonucleotides.

Advances in molecular biology and synthetic chemistry over the past two decades have stimulated interest in developing antisense oligonucleotides as therapeutic agents. It would be beneficial to develop an antisense oligonucleotide based therapy for breast cancer to provide targeted immunotherapy.

Insulin-Like Growth Factor and its Receptor

Growth factors and their receptors are examples of molecular switches whose activation transduces a signal to the cell nucleus that enables growth, transformation and protection from cell death. Insulin-like growth factor 1 (IGF-1) and its receptor (IGF-1R) appear to be required for mitosis in many cell types. In vitro, most cells in culture are dependent on IGF-1 for growth, and many tumor lines secrete IGF-1 and express IGF-1R. IGF-1R is required for the entry of stimulated lymphocytes and HL-60 cells into S Phase. In the absence of proliferation, such as in senescent human fibroblasts, IGF-1 mRNA is not detectable by reverse transcriptase polymerase chain reaction. Once these senescent cells are transfected with a temperature sensitive SV40 T antigen gene, they regain the ability to express IGF-1 mRNA at permissive temperatures. IGF-1R is also associated with growth in vivo. Mice with homozygous null mutations for igf-1r gene die shortly after birth with a body weight 30% of wild type.

The expression of IGF-1R may be required for transformation in vitro and for tumor maintenance in vivo. When the gene encoding IGF-1R is disrupted in mouse embryo fibroblasts, transformation by either Ha-ras, SV40 tumor antigen or both, is prevented. The transformed phenotype is restored once cells are transfected with a plasmid expressing the IGF-1R RNA. Overexpression of the IGF-1R results in increased transformability of NIH 3T3 cells. Not only is oncogenesis associated with the induction of IGF genes, but preliminary data suggests that the gene product of the retinoblastoma tumor suppresser gene inhibits the expression of the IGF-1 gene.

The IGF-1 receptor (IGF-1R) is a membrane glycoprotein composed of two alpha (Mr 130,000) and two beta (Mr 98,000) subunits linked together by disulfide bonds. The alpha subunit binds IGF-1 and IGF-2 with equal affinity. The β-subunit has an intracellular domain with tyrosine kinase activity which upon activation by either IGF-1 or IGF-2 autophosphorylates its own β-subunit and two major substrates, insulin receptor substrate 1 and Shc. Once activated, IGF-1R transmits a signal, transduced through ras and raf, to the nucleus. IGF-1 is known to stimulate the expression of approximately 30 genes expressed in 3T3 cells, encoding both cytoplasmic and nuclear proteins.

Within one minute of IGF-1R ligand binding, a series of other cellular proteins as well as nuclear proteins including the 43 kD product of the c-jun protooncogene, are also phosphorylated in vitro.

The IGF-1R is required for the action of several growth factors. Antisense to IGF-1R blocks the EGF stimulated proliferation of 3T3 cells overexpressing EGFR. Neither PDGFR nor EGFR antisense inhibit IGF-1 stimulated growth in cells overexpressing IGF-1R. There is evidence that other protooncogenes, such as c-myb, induce expression of IGF-1 and IGF-1R. When c-myb is overexpressed in fibroblasts, the IGF-1 requirement for growth is lost because both IGF-1 and IGF-1R mRNA is induced. When c-myb expression is inhibited, there is a decrease in the IGF-1R mRNA. However, inhibition of IGF-1R expression has no effect on the c-myb mRNA levels.

IGF-1R antisense can inhibit the growth of cells whose growth depends on expression of IGF-1R. Cells that are exposed to IGF-1R antisense and cells that are transfected with a viral vector expressing IGF-1R antisense show diminished levels of IGF-1R protein. This results in growth inhibition in IGF-1R dependent cells like rat C6 glioblastoma cells, an IGF-1R dependent tumor cell line. Diminished tumorogenicity results from transfection of C6 glioblastoma cells with a viral vector expressing IGF-1R antisense. For example, no tumors developed in rats injected with C6 glioblastoma cells bearing a viral vector expressing IGF-1R antisense. Injection with these antisense-transfected cells can also protect rats from glioblastoma tumor formation due to subsequent injection of wild type C6 glioblastoma cells. No tumors appeared in 4 weeks after the injection of the wild-type cells. Injection of the antisense-transfected C6 glioblastoma cells also caused regression of previously established wild-type C6 glioblastoma tumors. In each of these experiments the cells that exhibited diminished tumorogenicity or that affected tumor growth were transfected with a viral vector to express IGF-1R antisense.

Work, to date, studying IGF-1R antisense in cancer cells has been performed by transfecting cells with antisense DNA integrated in a viral vector. The consequences of inserting viral DNA into human gliomas are unknown. An estimated 23 human years of retroviral mediated gene transfer has been performed in humans without known side effects, although some of the viral vectors being used for gene therapy have the long-term potential for causing cancer. Side effects have been described in 3 monkeys at the NIH, who developed malignant T cell lymphoma after bone marrow transplant and gene transfer with a helper virus contaminated retrovirus. Aside from the potential side effects and risks of viral contamination, using viral vectors to transfect each tumor line with antisense is very labor intensive.

The practical use of antisense genetic therapy would be greatly enhanced by incorporation of antisense oligonucleotides into the breast, or other, tumor cells without the use of a retroviral vector. In light of the present shortcomings in breast cancer therapy, it would be advantageous to have a therapy that specifically inhibited the growth and metastasis of breast cancer cells without the side effects of present therapies. Antisense oligonucleotides present one avenue for such therapy, but present methods for treatment with antisense oligonucleotides require viral vectors and have not proven effective in inhibiting the growth and metastasis of breast cancer cells. Hence, there is a need for an antisense-oligonucleotide based therapy for breast cancer that eliminates use of viral vectors.

SUMMARY OF THE INVENTION

The present invention includes a therapeutic composition useful for inhibiting the growth of breast cancer cells. The composition includes a tumor cell immunogen derived from breast cancer cells that have been treated with an IGF-1 receptor antisense oligonucleotide. Preferably, the treated breast cancer cells are inactivated, e.g., not viable.

The preferred immunogen is an inactivated cancer cell treated with IGF-1 receptor antisense oligonucleotide (AON). The immunogen can include whole cells, cell membranes, lysates or extracts of cancer cells treated with IGF-1R antisense oligonucleotide.

The antisense oligonucleotide used to produce the immunogen is complementary to the gene or mRNA of the insulin-like growth factor type 1 receptor (IGF-1R). Preferably, the IGF-1R antisense oligonucleotide is about 14 to about 25 nucleotides in length. More preferably, the IGF-1R antisense oligonucleotide has a sequence complementary to the nucleotide sequence of the human IGF-1R precursor signal sequence, complementary to the nucleotide sequence at or near the initiation site, or complementary to sequence the nucleotide at or near a site for ribosome complex assembly.

More preferably, the sequence of the IGF-1 receptor antisense oligonucleotide contains the following sequence:

```
5' TCC TCC GGA GCC AGA CTT 3'  (AON1)   [SEQ ID NO:1], or
5' ACT CGT CGG CCA GAG CGA GAG 3' (AON2)  [SEQ ID NO:2].
```

Advantageously, the IGF-1 receptor antisense oligonucleotide is modified, for example, by including synthetic bases or modifying the backbone, such as by substituting phosphothioates or phosphonates.

The invention also includes a method of preparing a therapeutic composition by treating breast cancer cells with an IGF-1 receptor antisense oligonucleotide.

Another embodiment of the invention is a tumor cell immunogen derived from a breast cancer cell treated with an IGF-1 receptor antisense oligonucleotide.

A further embodiment of the invention is an IGF-1 receptor antisense oligonucleotide having the sequence:

5' ACT CGT CGG CCA GAG CGA GAG 3' (AON2) [SEQ ID NO:2].

The invention also includes using the tumor cell immunogen in a method of immunizing a breast cancer patient; in a method of inhibiting growth of breast cancer cells; in a method of inhibiting metastasis of breast cancer cells, including the inhibition of breast cancer cell metastasis behind the blood-brain-barrier; and, in a method of treating breast cancer. Each of these methods includes administering to a patient a tumor immunogen produced by treating breast cancer cells with an IGF-1 receptor antisense oligonucleotide and thereby inducing an anti-tumor response.

BRIEF DESCRIPTION OF THE FIGURES

FIG. 6 shows the nucleotide sequence of the cDNA clone of the IGF-1 receptor [SEQ ID NO:4] and the predicted amino acid sequence as reported by Ullrich et al., *EMBO J* 5:2503–2512 (1986). The α subunit includes the amino acids numbered 31–740, the putative precursor processing sequence is at amino acids 737–740, and the β subunit amino acids 741–1367. Amino acids 1–30 are a 30 residue signal sequence. Amino acids 936–959 are believed to form a transmembrane domain.

DETAILED DESCRIPTION OF THE PREFERRED EMBODIMENTS

Antisense Oligonucleotides

Figure 1:
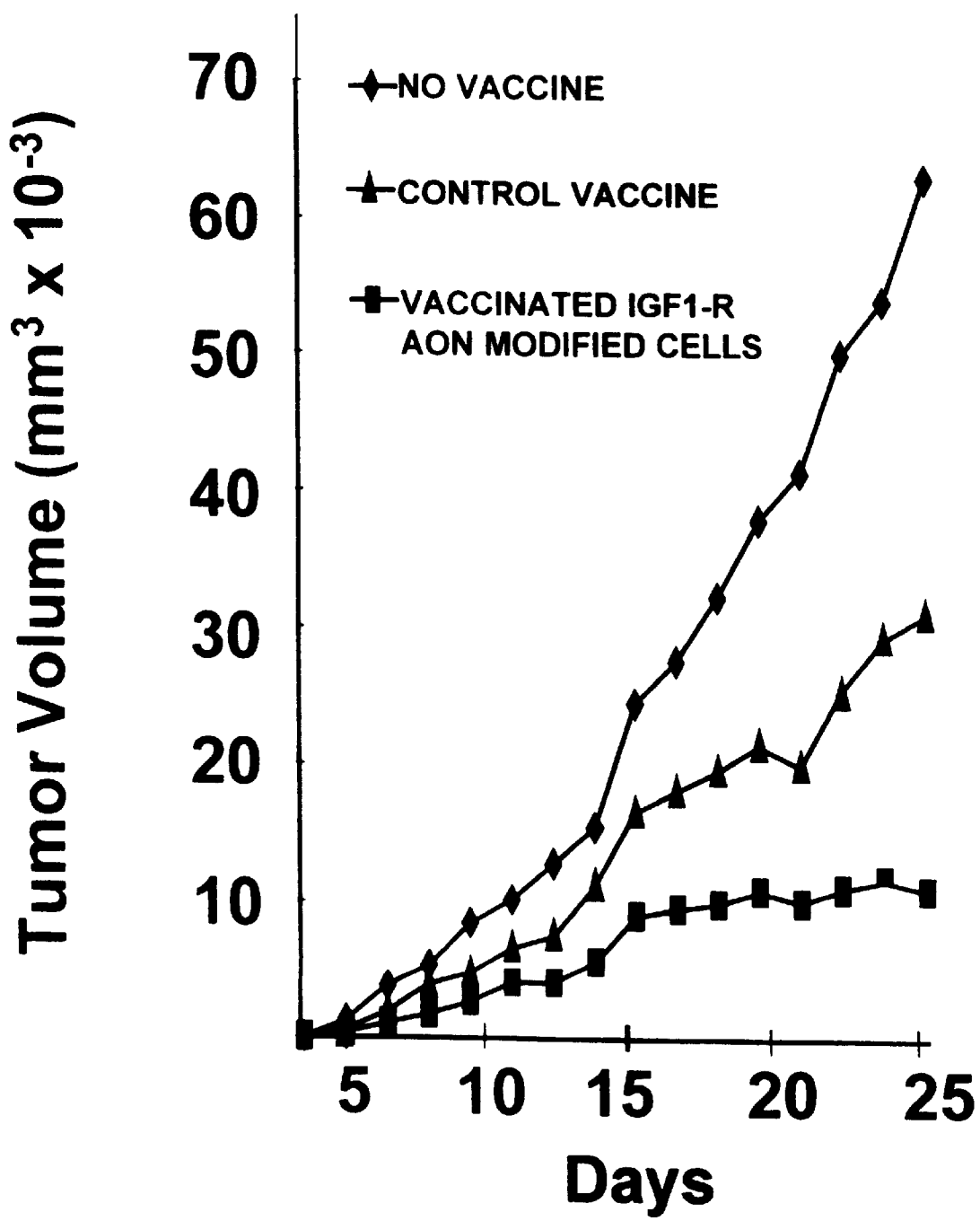
FIG. 1 is a graph showing the effects of treatment with irradiated cells pretreated with IGF-1 receptor antisense oligonucleotide AON1 on tumor volume in rats with MAT3B breast tumors.

Antisense oligonucleotides are nucleotide sequences that are complementary to specified segments of a targeted gene or mRNA. In the present invention, an IGF-1 receptor antisense oligonucleotide is complementary to a segment of the IGF-1 receptor gene, or to IGF-1 receptor mRNA.

The antisense oligonucleotides of the invention are preferably about 14–25 nucleotides in length. Most preferably, the oligonucleotides are about 15–20 nucleotides in length. It has been estimated that an antisense oligonucleotide containing at least 14 bases is required to specifically target a unique mammalian gene sequence, so longer oligonucleotides can provide greater specificity for targeting a specific sequence. However, small oligonucleotides are advantageous because they are typically more readily taken up by cells and can exhibit improved absorbtion and like properties. Thus, the most preferred size, 15–20 nucleotides, is chosen to balance target specificity and improved uptake by cells. The preferred oligonucleotide sequence can form Watson-Crick type base pairs along the entire target sequence, but less base pairing can be tolerated when advantageous cellular uptake, pharmacokinetics, or metabolism and adequate target recognition result from the altered sequence.

The particular sequence of the nucleotides provides the molecule with the specificity for targeting genetic material, such as DNA or mRNA. The antisense oligonucleotides of the invention have sequences that are complementary to the IGF-1 receptor gene or mRNA. Preferred oligonucleotides are those that are complementary to a sequence encoding the IGF-1 receptor precursor signal peptide, to sequences at or near the initiation site (AUG codon), or those sequences at or near a site for ribosome complex assembly, a site at which a ribosome binds to a polynucleotide. A sequence is near a site on an oligo- or polynucleotide if a complementary sequence would overlap with or interfere with the function of the site.

Most preferred antisense oligonucleotides of the invention are oligonucleotides AON1 [SEQ ID NO:1] and AON2 [SEQ ID NO:2] having the nucleotide sequences shown above. The antisense oligonucleotides can be produced by known, standard methods including chemical synthesis.

The antisense oligonucleotides of the invention can be chemically modified, such as by including synthetic bases or by modifications of the phosphate or sugar backbone. Such chemical modification can increase the stability and biological half-life of these compounds by reducing sensitivity to degradation by exonucleases, such as 3'-exonucleases, and endonucleases. Preferred are modifications that affect the phosphate backbone such as phosphorothioate-, phophorodithioate-, methylphosphonate-, and phosphoramidite modified oligomers, as these are stable and typically resistant to degradation by nucleases. The biological half-life of a phosphorothioate antisense sequence, for example, has been determined to be approximately 48 hours. The ribose moiety of the sugar backbone can be modified as well. For example, 2'-methyl-ribonucleotides and alpha-anomer nucleotides can be incorporated into the antisense oligonucleotides. Production and properties of modified oligonucleotides is described in *"Oligonucleotides—Antisense Inhibitors of Gene Expression"*, J. S. Cohen ed., CRC Press, Inc., Boca Raton, Fla. (1989).

The amount of antisense oligonucleotide required in the treatment of breast tumor cells is an amount effective to increase the activity of the breast tumor cells as tumor immunogen. Preferably, the antisense oligonucleotide is effective to produce an immunogen of potency such that a subject can be inoculated with an equivalent of about $2.5 \times 10^9$ treated cells per 75 kg person. In preparing the immunogen of the invention about $30 \times 10^6$ cells are incubated in a solution of about 5 μM to about 80 μM antisense oligonucleotide, more preferably about 10 μM to about 40 μM antisense oligonucleotide. The antisense oligonucleotide can be added to cells in suspension or culture, in cell culture medium or another vehicle.

Mechanisms of Antisense Action

In the present invention, treatment of breast tumor cells with an IGF-1 receptor antisense oligonucleotide modifies the tumor cells to produce a breast tumor immunogen. Such a modified breast tumor cell is a preferred tumor immunogen for use to inhibit the growth of breast cancer cells.

Although not limiting to the present invention, there are several mechanisms that can account for production of such an immunogen. For example, treatment with the antisense oligonucleotide could result in a change in phenotype of the treated cell, so the cell becomes a tumor immunogen. Alternatively, gene expression could be altered with resulting increased expression or display of an antigen or immunogen to breast tumor on the treated cells. It is believed that binding of an antisense oligonucleotide to DNA or RNA within a cell can inhibit translation and transcription, which can disrupt gene expression.

Several theories have been advanced to explain the general action of antisense oligonucleotides in a variety of systems. Proposed mechanisms of action for antisense oligonucleotides can be classified as passive, reactive, and activating. Passive blocking of function occurs by steric hindrance whereby an mRNA molecule cannot effectively interact with ribosomes, or is unable to pass from the nucleus to the cytoplasm. Reactive processes occur where antisense oligonucleotides bind directly with a target sequence and either block its action or cause its cleavage.

For example, binding of antisense oligonucleotides to target DNA can interrupt gene transcription, or if the antisense oligonucleotide binds to mRNA, translation will be disrupted. Consequently, the synthesis of a particular protein product can be inhibited. In cell-free translation systems, the best mRNA target sites are considered the 5' end (at or near the initiation AUG codon) and at or near the sites for ribosome complex assembly. Cleavage is advantageous because it destroys the target DNA or RNA. In addition, when a target DNA or RNA is cleaved, the antisense oligonucleotide will be released intact to recycle and bind to other target sequences. The activating mechanisms of RNase H result in the digestion of the target mRNA irrespective of the point of antisense attachment.

Modification of the antisense oligonucleotide can have advantageous effects on the mechanism or action of the antisense oligonucleotide. For example, phosphodiester antisense oligonucleotides hybridize very efficiently to complementary RNA sequences and thereby block translation, but they also can recruit the enzyme RNase H which cleaves the RNA component of the RNA/DNA duplex. Methylphosphonate antisense oligonucleotides are readily taken up by cells, have low toxicity and high stability, however, they hybridize poorly and may not induce the activity of RNase. Phophorothiaoate antisense oligonucleotides, in contrast, hybridize efficiently and induce RNase in a concentration-dependent fashion. Based on these theories of action, phosphorothioate antisense oligonucleotides with resistance to endonuclease activity can be advantageous in the immunogens and methods of the invention.

Treated Tumor Cells

Tumor immunogen of the present invention is preferably whole tumor or cancer cells that have been treated with an antisense oligonucleotide complementary to the IGF-1 receptor gene or mRNA. Immunogen, as used herein, refers to a substance that can induce an immune response, including either a humoral and/or cellular immune response. The tumor immunogen may also be derived from treated tumor cells by subjecting them to processes such as altering growth media, washing, purification, isolation, freezing, inactivation, lysis, extraction, and the like.

Treatment can include a single dose or multiple doses of antisense oligonucleotide. Preferably, the tumor cells are treated with two doses of antisense oligonucleotide. Typically, when treatment includes two doses of oligonucleotide, one dose of antisense is added at the beginning of the incubation and a second is added about half way through the incubation. Preferably, for treatment, the cells are incubated with antisense oligonucleotide for about 23 hours, then maintained in culture for about one to two hours prior to use as a vaccine or immunogen, or before further processing. Treatment of cells is preferably under culture conditions favorable for the tumor cell type, generally at a temperature of 37° C. and in a nutrient medium such as RPMI cell culture medium.

After treatment with antisense oligonucleotide, the treated cells are inactivated, preferably by irradiation. Treated, inactivated cells are preserved by methods, such as quick freezing at −80° C., that maintain the immunogenicity of the stored cells. This process yields tumor immunogen derived from treated breast cancer cells. The conditions of culture and incubation with the antisense oligonucleotide can be chosen to provide for effective production of tumor immunogen.

The tumor immunogen is preferably prepared from a specific patient's tumor, e.g. from biopsy tissue or from explants of a removed tumor, or from cell culture of the patient's tumor cells. A patient's breast tumor cells can be obtained by standard biopsy methods. Cells from excised tumor tissue can be used directly, or alternatively, cells from the excised tumor can be cultured and expanded under standard culture conditions to produce increased numbers of cells. Tumor cells from a patient can also be used to establish a permanent tumor cell line that can then be treated to make the immunogen of the invention, the immunogen or vaccine of the invention, or used in the methods of the invention.

Tumor cells are preferably inactivated, e.g., by methods known in the field, the most common method being irradiation as described in the examples below. Other known inactivation methods include oxygen deprivation, use of plant and animal toxins, and chemotherapeutic agents. In an alternative embodiment, lysed tumor cells may be used as the tumor immunogen, as well as cell membranes and specific tumor cell protein immunogens; however, inactivated whole tumor cells are preferred.

For administration, the tumor immunogen is suspended in an aqueous medium such as phosphate buffered saline. The amount of tumor immunogen administered is that sufficient to induce an immune response. In rat studies, administration of $5 \times 10^6$ irradiated tumor cells in 300 μL phosphate buffered saline was efficient in preventing tumor growth. Thus, the expected useful human dose of irradiated tumor cells for a subcutaneous injection is about $2.5 \times 10^9$ cells per 75 kg person. Administration of other types of tumor immunogens, e.g. cell membrane or purified tumor cell immunogens, are administered to deliver a like amount of immunogen.

The therapeutic composition of the invention includes tumor cell immunogen in a form suitable for administration to a patient. For example, the composition can include adjuvants, cofactors and pharmaceutically acceptable carriers, vehicles, or buffers, and the like to formulate the composition for administration to a patient. The therapeutic composition can include one or more forms of the tumor cell immunogen in quantities effective to stimulate an immune response in the patient. The therapeutic composition of the invention can formulated and administered as a vaccine. Vaccine, as used herein, refers to a therapeutic composition formulated for administration to prevent, ameliorate, or treat a disease, such as cancer.

Methods of Administering

For the vaccine, immunogen and methods of the invention, administration of breast tumor immunogen for inhibiting the growth of breast cancer cells and the treatment of breast tumors is to a peripheral site, preferably by subcutaneous injection. Preferred peripheral sites for administration include the upper arm, thigh, and trunk areas of the body.

Timing of tumor immunogen administration is as needed to produce immune reactivity, and can be monitored by assessing change in tumor size (e.g., by MRI), immune response (e.g., by delayed type hypersensitivity skin test), and by measuring interferon-gamma secretion by the patient's TH-1 cells in response to tumor immunogen. Treatment is preferably continued until immune response is detected and/or tumor ablation is achieved.

Patient Populations

Patients at risk of or suffering from all types of breast tumors are treated by the method of the invention. A successful peripheral administration of tumor immunogen for the treatment of breast tumor is surprising, given the distant location of the tumors. The claimed method of treating with breast cancer tumor immunogen is particularly useful in preventing tumor recurrence, for example, after tumor reduction techniques, such as surgical debulking removal, irradiation, and/or chemotherapy.

Treating breast cancer tumors can also result in inhibition of growth of breast tumor cells, tumor regression, delay in or slowing of tumor growth, reduction in tumor mass, and other beneficial effects on tumor progression. Inhibiting growth of breast tumor cells includes slowing division or killing the cells. Inhibited cell growth leads to slower tumor growth, which depends on growth of individual cells. Treating or preventing metastasis includes stopping, slowing, or delaying the spread of the breast cancer tumor cells to other tissues or organs in the patient. Preventing breast cancer in a patient refers to treatment of patients at risk of breast cancer to delay or prevent the onset of breast cancer. Prevention can be measured as a reduction of incidence of breast cancer in a population at risk of breast cancer. Alternatively, preventing cancer in breast cancer survivors includes inhibiting recurrence or regrowth of breast cancer. Administration of the therapeutic composition of the invention effectively inhibits regrowth of tumor, e.g. from residual tumor cells.

EXAMPLES

The invention will be further described by reference to the following detailed examples, which are exemplary in nature and not intended to limit the scope of the invention.

Example 1

Vaccination with Breast Tumor Cells Treated with IGF-1Receptor (AON1) Antisense Oligonucleotide Two IGF-1 receptor antisense oligonucleotides have been used to produce tumor cell immunogens for the inhibition of breast cancer growth. The first sequence used was a known antisense sequence, AON1 [SEQ ID NO:1], complementary to the nucleotide sequence of codons $-29$ to $-24$ (nucleotides $-87$ to $-70$) of the human IGF-1R precursor signal sequence. The sequence of AON1 is:

5' TCC TCC GGA GCC AGA CTT 3'

The second antisense oligonucleotide tested is AON2, [SEQ ID NO:2] described more fully below in Example 2, and having the following sequence:

5' ACT CGT CGG CCA GAG CGA GAG 3'

Vaccine Production

To provide tumor immunogens for immune stimulation, MAT3B cells were grown at 37° C. until reaching 80–90% confluence in 175 mm$^3$ flasks of DMEM media supplemented with glycine, penicillin, streptomycin and 10% fetal calf serum. These cells were then collected, centrifuged at 1000 g×5 minutes, washed twice in ice cold PBS, centrifuged and resuspended in each of three 175 mm$^3$ flasks in 10 mls of serum free DMEM media supplemented with 12.5 $\mu$M IGF-1 (Upstate Biotechnology), 0.10% BSA and 10 $\mu$M FeSO$_4$.

These three flasks were used to make cells for an antisense oligonucleotide treatment, a treatment with nonsense oligonucleotide, and a vehicle control treatment. Antisense treated cells were incubated with 12 $\mu$M IGF-1R AON (NBI, Plymouth, Minn.) in the first flask. Nonsense treated cells were incubated with 12 $\mu$M IGF-1R NON in the second flask. For the vehicle control treatment, an volume of oligonucleotide buffer (PBS) equivalent to the volume used in the other flasks was added to a third flask. Cells under treatment were incubated for 24 hours and redosed with 6 $\mu$M IGF-1R AON, 6 $\mu$M IGF-1R NON, or oligonucleotide buffer (PBS) during the last hour of incubation prior to harvest.

The Mat3B cells were then harvested, counted with a hemocytometer, resuspended in PBS at a concentration of $10^6$ per 300 $\mu$l PBS, and irradiated with 6000 rads$^{137}$ Cs. Irradiated cells were then quick frozen in liquid nitrogen and stored at $-70°$ C. until use (storage time varied between 0 and 48 hours).

Animal Vaccination

Female Fischer 344 rats, 150–160 gm and syngeneic for Mat3B cells, were obtained from Harlan (Indianapolis, Ind.) and cared for according to the University of Minnesota guidelines. Animals were either unvaccinated controls or vaccinated with Mat3B cells treated with IGF-1R AON, IGF-1R NON, or oligonucleotide buffer (PBS) as described under vaccine production. One of two vaccination protocols were used. For AON1 treated breast tumor cells, animals were vaccinated with subcutaneous hind limb injections of treated cells at 2 months and 1 month prior to tumor challenge. For AON2 or nonsense oligonucleotide treated breast tumor cells, animals were vaccinated with subcutaneous hind limb injections of treated cells or at 6 weeks, 4 weeks and 2 weeks prior to tumor challenge. Animals were vaccinated with 5×10$^6$ cells in 300 $\mu$l of PBS.

Peripheral Tumor Inoculation and Evaluation

To establish a model in which tumor growth or regression could be easily quantitated on a daily basis peripheral breast cancers were then established in the opposite hind flank of the vaccinated, or unvaccinated syngeneic rodents described above. Peripheral tumors were established by injecting 10$^6$ unmodified log phase Mat3B cells that had been harvested, washed and resuspended in 300 $\mu$l PBS.

Tumor lengths and widths were then measured daily by an observer who was blinded to the vaccination group. Tumor volumes were approximated using the equation $[(\text{width})^2 \times \text{length}]/2$, and averages± SEM were calculated daily for each group. Daily average tumor volumes from each group were compared over the course of the experiment using ANOVA and post hoc TUKEY with the SAS statistical analysis program. Groups averages were not compared after one or more animals in the group died or after all animals in the vaccination group recovered from their tumors.

Those rats which were resistant to or recovered from peripheral breast cancer were then monitored without further treatment for 2 months (AON2 or NON vaccination) to 7 months (AON1 vaccination). The tumor free rats were then rechallenged with peripheral breast cancer inoculations as above.

Results

FIG. 1 shows the effect of vaccination with AON1-treated tumor cells on breast tumor volume. Both unvaccinated naive animals and animals tested with phosphate buffered saline (PBS) treated cells exhibited rapid tumor growth. In contrast, animals immunized with AON1-treated tumor cells exhibited a significant delay in tumor growth. In this latter group two animals displayed a regression of tumor volume and a third animal never developed a palpable tumor.

Figure 2:
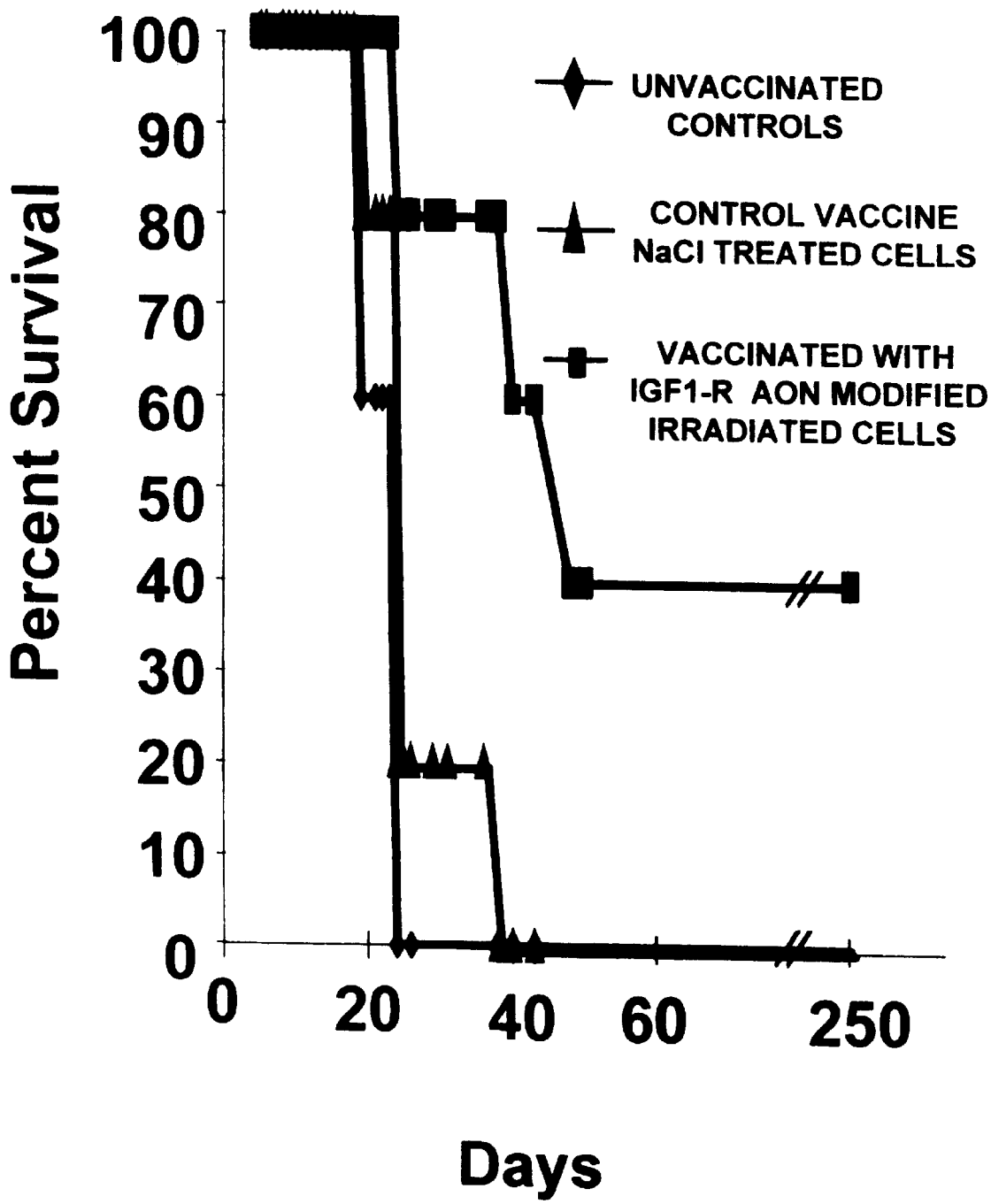
FIG. 2 is a graph showing the effect of treatment with irradiated cells pretreated with IGF-1 receptor antisense oligonucleotide AON1 on survival of rats with MAT3B breast tumors.

The survival of animals vaccinated with irradiated AON1 treated MAT3B tumor cells is shown in FIG. 2. Naive control animals all died within 25 days of breast tumor implantation. Animals vaccinated with NaCl treated cells all died within 38 days. In contrast, 40% of animals with IGF-1 receptor antisense (AON1) vaccinations survived beyond 250 days post tumor implantation and continue to survive.

These studies demonstrate IGF-1Receptor antisense oligonucleotide (AON1) when incubated with breast tumor cells produces a vaccine that prevents breast tumor cell growth in vaccinated animals.

Example 2

Vaccination with Breast Tumor Cells Treated with IGF-1 Receptor (AON2) Antisense Oligonucleotide A second antisense sequence IGF-1R AON2 was designed using a selected region of the IGF-1R gene sequence having the following sequence:

5' ACT CGT CGG CCA GAG CGA GAG 3' [SEQ ID NO:2]

A nonsense sequence used as a control having the following sequence:

5' TGG CAC CGT ACC AGG AGG CAG 3' [SEQ ID NO:3]

The IGF-1R AON2 sequence is complementary to a region of the IGF-1R gene that is homologous between humans, mice, and rats:

```
...GCGCTCTCGCTCTGGCCGACGAGTGGAGAAATCTGC....Human [nucleotides 112-137 of SEQ ID NO:4]
...GCGCTCTCGCTCTGGCCGACGAGTGGAGAAATTTGT....Mouse [nucleotides 112-132 of SEQ ID NO:4]
...GCGCTCTCGCTCTGGCCGACGAGTGGAGAAATTTGT....Rat [nucleotides 112-132 of SEQ ID NO:4]
```

Breast tumor cell vaccines were prepared as described in Example 1 by incubating MAT3B cells with the IGF-1 receptor antisense oligonucleotide AON2. Control vaccines were prepared by incubating MAT3B cells with the nonsense oligonucleotide (NON) and with PBS treated cells were irradiated, as described for Example 1. Syngeneic animals were immunized with the treated irradiated cells at 6, 4, and 2 weeks prior to breast tumor cell implantation, as described in Example 1. Peripheral tumors were established and evaluated as described in Example 1.

Results

Figure 3:
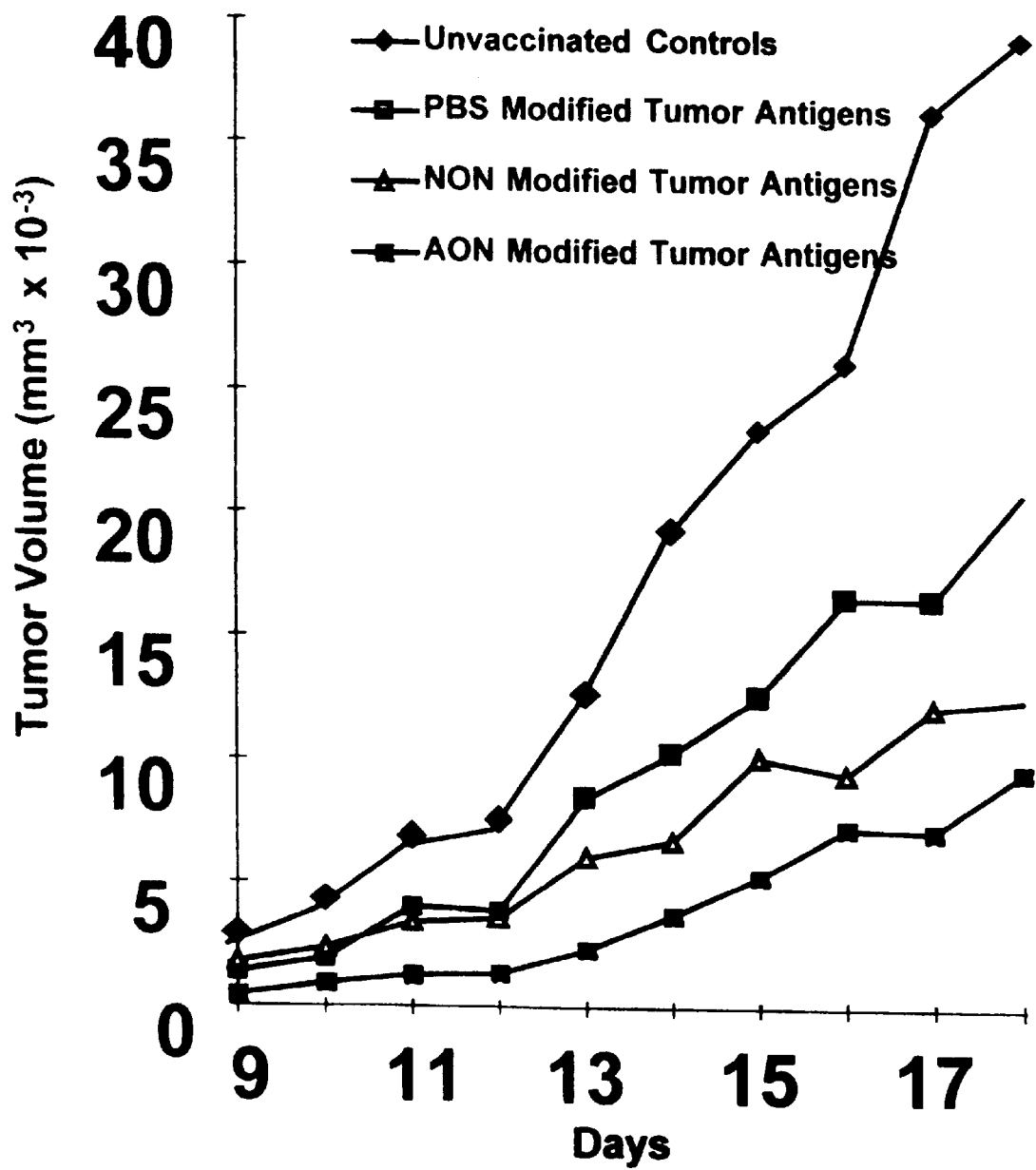
FIG. 3 is a graph showing the effect of treatment with irradiated cells pretreated with IGF-1 receptor antisense oligonucleotide AON2 on tumor volume in rats with MAT3B breast tumors.

The effects of this vaccine, AON2-treated tumor cells, on breast tumor growth is shown in FIG. 3. Unvaccinated control animals exhibited rapid breast tumor growth as did animals vaccinated with PBS-incubated cells. Animals vaccinated with tumor cells treated with the nonsense oligonucleotide, IGF-1R NON, displayed a slightly slower growth rate of the tumor. The slowest tumor growth rate was exhibited by animals vaccinated with tumor cells treated with the novel antisense oligonucleotide, AON2. One animal in this latter group had no palpable tumor, and one other animal exhibited a regression of its tumor.

Figure 4:
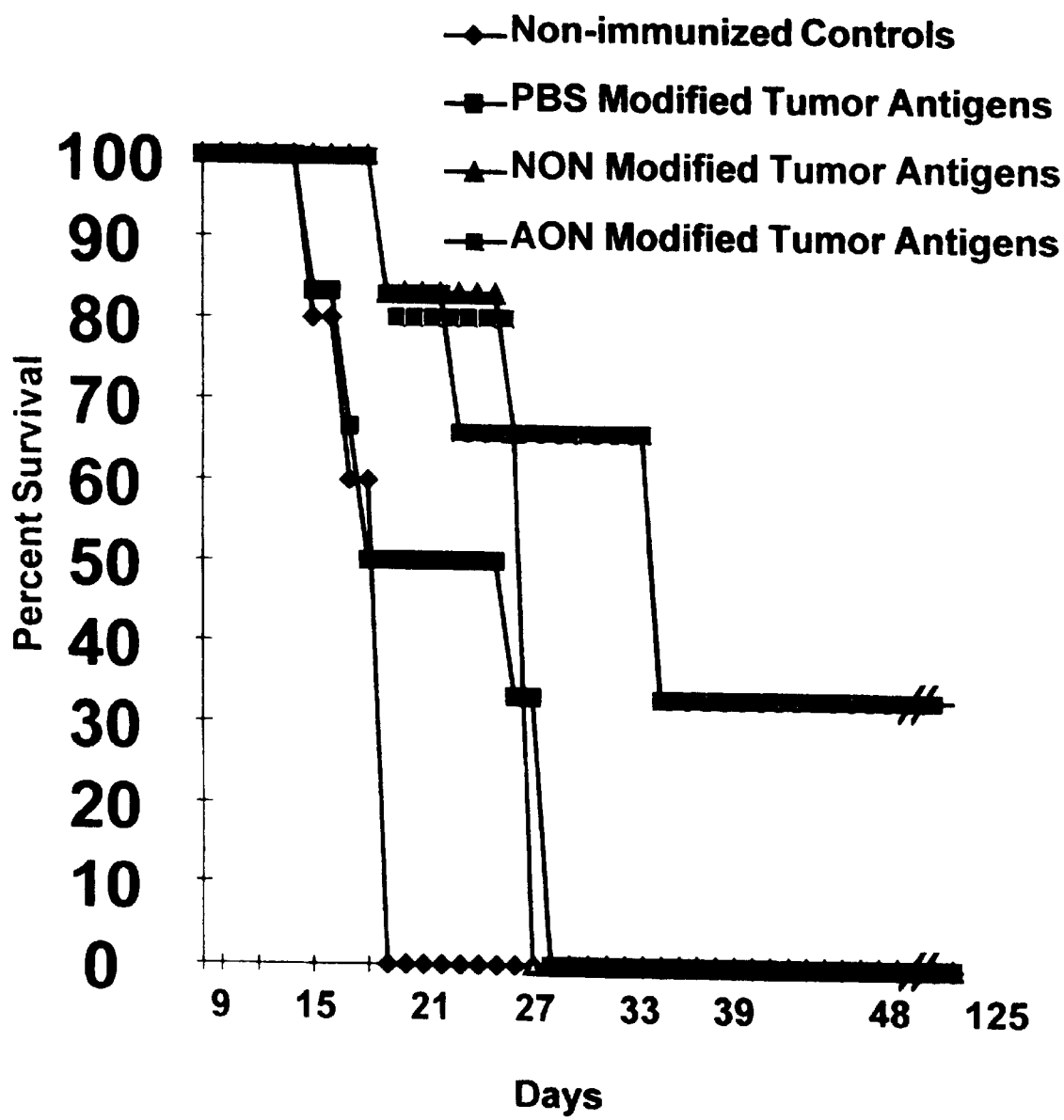
FIG. 4 is a graph showing the effect of treatment with irradiated cells pretreated with IGF-1 receptor antisense oligonucleotide AON2 on survival of rats with MAT3B breast tumors.

The survival of animals vaccinated with AON2-treated cells is shown in FIG. 4. Untreated control animals died within 19 days after breast tumor implantation. Animals vaccinated with PBS-treated cells or cells treated with nonsense oligonucleotide all succumbed to their cancer by day 28. In contrast, 33% of the animals vaccinated with AON2-treated cells have survived beyond 125 days and continue to survive.

These studies demonstrate IGF-1Receptor antisense oligonucleotide (AON2) incubated with breast tumor cells produces a vaccine that inhibits breast tumor cell growth in immunized animals.

Example 3

The Effect the AON1 Vaccine on Breast Tumor Metastasis to the Brain

The therapeutic effects of animal vaccination with IGF-1 receptor antisense oligonucleotide treated cells were also examined in a model of breast tumor metastasis to the brain. Fischer 344 rats were vaccinated with either IGF-1R AON1- or AON2-treated irradiated MAT3B cells prepared and vaccinated as described above for Example 1.

Central Tumor Inoculation and Evaluation

In the model for breast cancer metastasis, 1 unmodified, log phase Mat3B cells were suspended in 10 $\mu$l PBS and injected into the striatum of vaccinated or unvaccinated syngeneic rats. To assess the length of protection provided by the vaccine, these animals were vaccinated 3 months (group 2) to 8 months (group 1) prior to intracerebral challenge.

Injections were made at the rate of 1 $\mu$l per minute with a 5 minute pause prior to removal of the Hamilton syringe. Animals were monitored for survival. In long term survivors, the presence or absence of tumors was assessed with MRI of animals anesthetized with ketamine/xylozine.

Results

Figure 5:
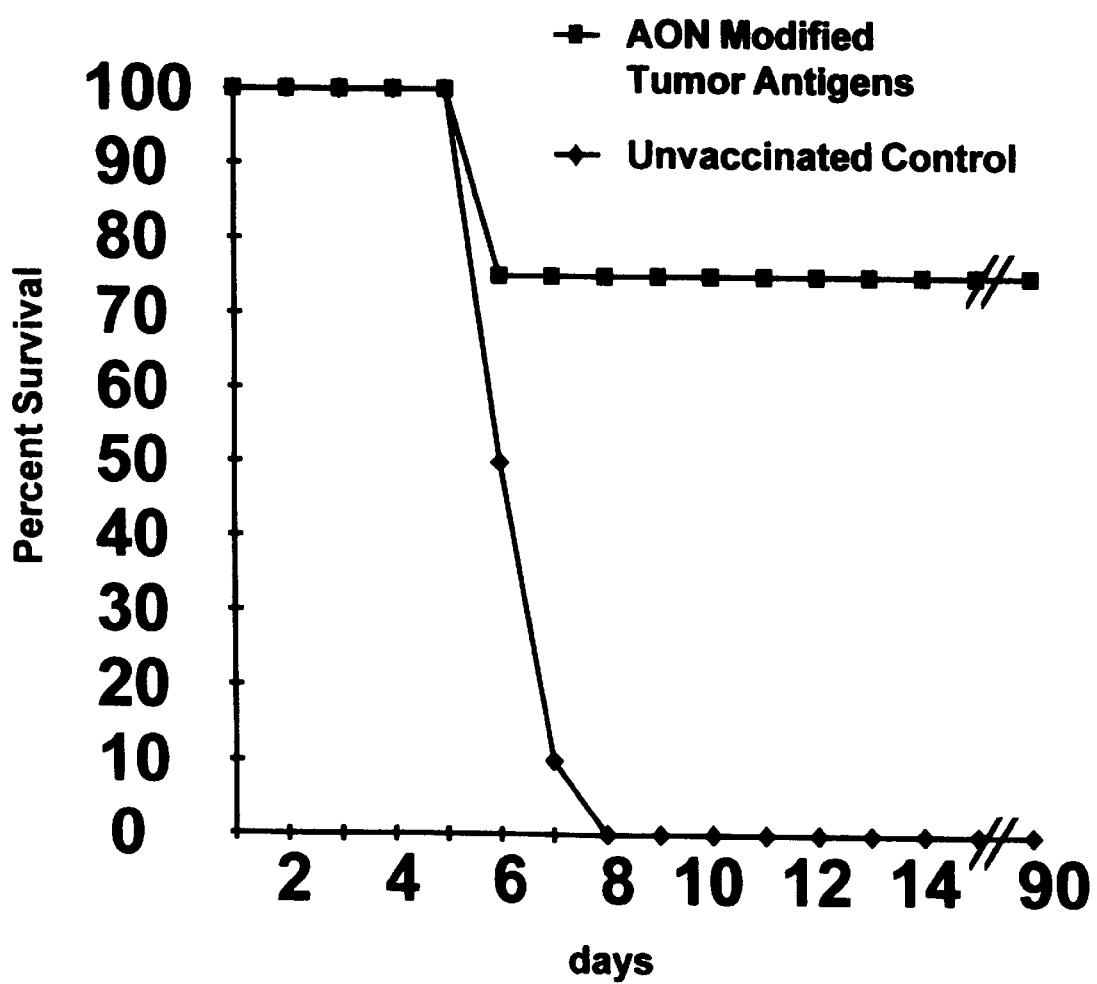
FIG. 5 is a graph showing the effect of treatment with irradiated cells pretreated with IGF-1 receptor antisense oligonucleotides AON-1 or AON-2 on survival of rats with intracerebral tumors of MAT3B breast tumor cells.

All control animals (n=10) died by day 8 after the intracerebral injections because of tumor growth within the brain (see Table 1 and FIG. 5). In contrast, 75% of the rats previously immunized with either IGF-1R AON1 or AON2-treated tumor cells survived 90 days beyond the intracerebral injection and continue to survive (FIG. 5). There was no significant difference between the animals treated with AON-1 or AON-2, and the data for these two treatments were pooled in the results reported in Table 1 and FIG. 5.

TABLE 1

| Survival of rats with intracerebral tumors of breast carcinoma cells | | |
|---|---|---|
| Non-immunized control rats | (0/10) | 0% |
| IGF-1R AON immunized rats | (3/4) | 75% |

MRI of immunized and non-immunized rats demonstrated the prevention of metastatic MAT3B breast tumor growth in the brain and the regression of tumors in vaccinated animals.

The invention has been described with reference to various specific and preferred embodiments and techniques. However, it should be understood that many variations and modifications may be made while remaining within the spirit and scope of the invention.

All publications and patent applications in this specification are indicative of the level of ordinary skill in the art to which this invention pertains. All publications and patent applications are herein incorporated by reference to the same extent as if each individual publication or patent application was specifically and individually indicated by reference.

We claim:

1. A therapeutic composition for inhibiting the growth of breast cancer cells, comprising:
breast cancer cells treated with an IGF-1 receptor antisense oligonucleotide, or an inhibitory portion of said treated breast cancer cells.

2. The composition of claim 1, wherein the oligonucleotide-treated breast cancer cells are inactivated.

3. The composition of claim 2, wherein the inactivated breast cancer cells are irradiated.

4. The composition of claim 1, wherein said breast cancer cells are obtained from a patient to be treated with the therapeutic composition.

5. The composition of claim 1, wherein the breast cancer cells are obtained from a permanent breast tumor cell line.

6. The composition of claim 1, wherein the IGF-1 receptor antisense oligonucleotide comprises about 14 to about 25 sequential nucleotides.

7. A therapeutic composition for inhibiting the growth of breast cancer cells, comprising:
breast cancer cells treated with an IGF-1 receptor antisense oligonucleotide comprising a sequence complementary to the nucleotide sequence of codons of the human IGF-1R precursor signal sequence, complementary to the nucleotide sequence at or near an initiation site, or complementary to sequences at or near a site for ribosome complex assembly, or an inhibitory portion of said treated breast cancer cells.

8. A therapeutic composition for inhibiting the growth of breast cancer cells, comprising:
breast cancer cells treated with an IGF-1 receptor antisense oligonucleotide comprising one or more of the following sequences:

```
5' TCC TCC GGA GCC AGA CTT 3' (SEQ ID NO:1) or
5' ACT CGT CGG CCA GAG CGA GAG 3' (SEQ ID NO:2)
``` or a inhibitory portion of said treated breast cancer cells.

9. The composition of claim 1, wherein the IGF-1R antisense oligonucleotide comprises one or more synthetic base or a modified backbone.

10. An anti-breast tumor vaccine comprising:
breast cancer cells treated with an IGF-1 receptor antisense oligonucleotide, or an immunogenic portion of said treated cells; and
a pharmaceutically acceptable carrier.

11. An IGF-1 receptor antisense oligonucleotide comprising the sequence:
5' ACT CGT CGG CCA GAG CGA GAG 3' (SEQ ID NO:2).

12. A method for inhibiting the growth of breast cancer cells in a patient, the method comprising:
administering to a patient breast cancer cells treated with an IGF-1 receptor antisense oligonucleotide, or an inhibitory portion of said treated cells.

13. The method of claim 12, wherein said administering is subsequent to or concurrent with tumor reduction therapy.

14. The method of claim 13, wherein said administering is subsequent to surgical debulking of tumors.

15. The method of claim 12, wherein the IGF-1 receptor antisense oligonucleotide comprises about 14 to about 25 sequential nucleotides.

16. The method of claim 12, wherein the IGF-1 receptor antisense oligonucleotide comprises a sequence complementary to the nucleotide sequence of codons of the human IGF-1R precursor signal sequence, complementary to the nucleotide sequence at or near an initiation site, or complementary to sequences at or near a site for ribosome complex assembly.

17. The method of claim 12, wherein the IGF-1 receptor antisense oligonucleotide comprises one or more of the following sequences:

```
5' TCC TCC GGA GCC AGA CTT 3' (SEQ ID NO:1) or
5' ACT CGT CGG CCA GAG CGA GAG 3' (SEQ ID NO:2).
```

* * * * *

UNITED STATES PATENT AND TRADEMARK OFFICE
CERTIFICATE OF CORRECTION

PATENT NO. : 6,071,891  
DATED : June 6, 2000  
INVENTOR(S) : Low et al.

It is certified that error appears in the above-identified patent and that said Letters Patent is hereby corrected as shown below:

<u>Title page</u>,  
<u>Item [75] Inventors</u>,  
Insert -- both of Minn -- after the word "Edina"  
Delete "Plymouth, all of Minn" after the name "Chiang,"  
Insert -- Longmont, Co. 80501 -- after the name "Chiang"

<u>Column 12</u>,  
Line 6, "1" should read -- $10^6$ --

Signed and Sealed this

Thirteenth Day of November, 2001

Attest:

NICHOLAS P. GODICI  
*Attesting Officer*   *Acting Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

TCCTCCGGAG CCAGACTT                                                      18

(2) INFORMATION FOR SEQ ID NO:2:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

ACTCGTCGGC CAGAGCGAGA G                                                  21

(2) INFORMATION FOR SEQ ID NO:3:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

TGGCACCGTA CCAGGAGGCA G                                                  21

(2) INFORMATION FOR SEQ ID NO:4:

-continued

```
  (i) SEQUENCE CHARACTERISTICS:
      (A) LENGTH: 4989 base pairs
      (B) TYPE: nucleic acid
      (C) STRANDEDNESS: single
      (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
      (A) NAME/KEY: Coding Sequence
      (B) LOCATION: 46...4149
      (D) OTHER INFORMATION:

(xi) SEQUENCE DESCRIPTION: SEQ ID NO:4:
```

```
TTTTTTTTTT TTTTGAGAAA GGGAATTTCA TCCCAAATAA AAGGA ATG AAG TCT GGC       57
                                                 Met Lys Ser Gly
                                                   1

TCC GGA GGA GGG TCC CCG ACC TCG CTG TGG GGG CTC CTG TTT CTC TCC       105
Ser Gly Gly Gly Ser Pro Thr Ser Leu Trp Gly Leu Leu Phe Leu Ser
 5              10              15                  20

GCC GCG CTC TCG CTC TGG CCG ACG AGT GGA GAA ATC TGC GGG CCA GGC       153
Ala Ala Leu Ser Leu Trp Pro Thr Ser Gly Glu Ile Cys Gly Pro Gly
            25                  30                  35

ATC GAC ATC CGC AAC GAC TAT CAG CAG CTG AAG CGC CTG GAG AAC TGC       201
Ile Asp Ile Arg Asn Asp Tyr Gln Gln Leu Lys Arg Leu Glu Asn Cys
        40                  45                  50

ACG GTG ATC GAG GGC TAC CTC CAC ATC CTG CTC ATC TCC AAG GCC GAG       249
Thr Val Ile Glu Gly Tyr Leu His Ile Leu Leu Ile Ser Lys Ala Glu
    55                  60                  65

GAC TAC CGC AGC TAC CGC TTC CCC AAG CTC ACG GTC ATT ACC GAG TAC       297
Asp Tyr Arg Ser Tyr Arg Phe Pro Lys Leu Thr Val Ile Thr Glu Tyr
 70                  75                  80

TTG CTG CTG TTC CGA GTG GCT GGC CTC GAG AGC CTC GGA GAC CTC TTC       345
Leu Leu Leu Phe Arg Val Ala Gly Leu Glu Ser Leu Gly Asp Leu Phe
85              90                  95                 100

CCC AAC CTC ACG GTC ATC CGC GGC TGG AAA CTC TTC TAC AAC TAC GCC       393
Pro Asn Leu Thr Val Ile Arg Gly Trp Lys Leu Phe Tyr Asn Tyr Ala
                105                 110                 115

CTG GTC ATC TTC GAG ATG ACC AAT CTC AAG GAT ATT GGG CTT TAC AAC       441
Leu Val Ile Phe Glu Met Thr Asn Leu Lys Asp Ile Gly Leu Tyr Asn
                120                 125                 130

CTG AGG AAC ATT ACT CGG GGG GCC ATC AGG ATT GAG AAA AAT GCT GAC       489
Leu Arg Asn Ile Thr Arg Gly Ala Ile Arg Ile Glu Lys Asn Ala Asp
                135                 140                 145

CTC TGT TAC CTC TCC ACT GTG GAC TGG TCC CTG ATC CTG GAT GCG GTG       537
Leu Cys Tyr Leu Ser Thr Val Asp Trp Ser Leu Ile Leu Asp Ala Val
        150                 155                 160

TCC AAT AAC TAC ATT GTG GGG AAT AAG CCC CCA AAG GAA TGT GGG GAC       585
Ser Asn Asn Tyr Ile Val Gly Asn Lys Pro Pro Lys Glu Cys Gly Asp
165                 170                 175                 180

CTG TGT CCA GGG ACC ATG GAG GAG AAG CCG ATG TGT GAG AAG ACC ACC       633
Leu Cys Pro Gly Thr Met Glu Glu Lys Pro Met Cys Glu Lys Thr Thr
                185                 190                 195

ATC AAC AAT GAG TAC AAC TAC CGC TGC TGG ACC ACA AAC CGC TGC CAG       681
Ile Asn Asn Glu Tyr Asn Tyr Arg Cys Trp Thr Thr Asn Arg Cys Gln
                200                 205                 210
```

```
AAA ATG TGC CCA AGC ACG TGT GGG AAG CGG GCG TGC ACC GAG AAC AAT       729
Lys Met Cys Pro Ser Thr Cys Gly Lys Arg Ala Cys Thr Glu Asn Asn
        215                 220                 225

GAG TGC TGC CAC CCC GAG TGC CTG GGC AGC TGC AGC GCG CCT GAC AAC       777
Glu Cys Cys His Pro Glu Cys Leu Gly Ser Cys Ser Ala Pro Asp Asn
        230                 235                 240

GAC ACG GCC TGT GTA GCT TGC CGC CAC TAC TAC TAT GCC GGT GTC TGT       825
Asp Thr Ala Cys Val Ala Cys Arg His Tyr Tyr Tyr Ala Gly Val Cys
245                 250                 255                 260

GTG CCT GCC TGC CCG CCC AAC ACC TAC AGG TTT GAG GGC TGG CGC TGT       873
Val Pro Ala Cys Pro Pro Asn Thr Tyr Arg Phe Glu Gly Trp Arg Cys
                265                 270                 275

GTG GAC CGT GAC TTC TGC GCC AAC ATC CTC AGC GCC GAG AGC AGC GAC       921
Val Asp Arg Asp Phe Cys Ala Asn Ile Leu Ser Ala Glu Ser Ser Asp
        280                 285                 290

TCC GAG GGG TTT GTG ATC CAC GAC GGC GAG TGC ATG CAG GAG TGC CCC       969
Ser Glu Gly Phe Val Ile His Asp Gly Glu Cys Met Gln Glu Cys Pro
        295                 300                 305

TCG GGC TTC ATC CGC AAC GGC AGC CAG AGC ATG TAC TGC ATC CCT TGT      1017
Ser Gly Phe Ile Arg Asn Gly Ser Gln Ser Met Tyr Cys Ile Pro Cys
        310                 315                 320

GAA GGT CCT TGC CCG AAG GTC TGT GAG GAA GAA AAG AAA ACA AAG ACC      1065
Glu Gly Pro Cys Pro Lys Val Cys Glu Glu Glu Lys Lys Thr Lys Thr
325                 330                 335                 340

ATT GAT TCT GTT ACT TCT GCT CAG ATG CTC CAA GGA TGC ACC ATC TTC      1113
Ile Asp Ser Val Thr Ser Ala Gln Met Leu Gln Gly Cys Thr Ile Phe
                345                 350                 355

AAG GGC AAT TTG CTC ATT AAC ATC CGA CGG GGG AAT AAC ATT GCT TCA      1161
Lys Gly Asn Leu Leu Ile Asn Ile Arg Arg Gly Asn Asn Ile Ala Ser
        360                 365                 370

GAG CTG GAG AAC TTC ATG GGG CTC ATC GAG GTG GTG ACG GGC TAC GTG      1209
Glu Leu Glu Asn Phe Met Gly Leu Ile Glu Val Val Thr Gly Tyr Val
        375                 380                 385

AAG ATC CGC CAT TCT CAT GCC TTG GTC TCC TTG TCC TTC CTA AAA AAC      1257
Lys Ile Arg His Ser His Ala Leu Val Ser Leu Ser Phe Leu Lys Asn
        390                 395                 400

CTT CGC CTC ATC CTA GGA GAG GAG CAG CTA GAA GGG AAT TAC TCC TTC      1305
Leu Arg Leu Ile Leu Gly Glu Glu Gln Leu Glu Gly Asn Tyr Ser Phe
405                 410                 415                 420

TAC GTC CTC GAC AAC CAG AAC TTG CAG CAA CTG TGG GAC TGG GAC CAC      1353
Tyr Val Leu Asp Asn Gln Asn Leu Gln Gln Leu Trp Asp Trp Asp His
                425                 430                 435

CGC AAC CTG ACC ATC AAA GCA GGG AAA ATG TAC TTT GCT TTC AAT CCC      1401
Arg Asn Leu Thr Ile Lys Ala Gly Lys Met Tyr Phe Ala Phe Asn Pro
        440                 445                 450

AAA TTA TGT GTT TCC GAA ATT TAC CGC ATG GAG GAA GTG ACG GGG ACT      1449
Lys Leu Cys Val Ser Glu Ile Tyr Arg Met Glu Glu Val Thr Gly Thr
        455                 460                 465

AAA GGG CGC CAA AGC AAA GGG GAC ATA AAC ACC AGG AAC AAC GGG GAG      1497
Lys Gly Arg Gln Ser Lys Gly Asp Ile Asn Thr Arg Asn Asn Gly Glu
        470                 475                 480

AGA GCC TCC TGT GAA AGT GAC GTC CTG CAT TTC ACC TCC ACC ACC ACG      1545
Arg Ala Ser Cys Glu Ser Asp Val Leu His Phe Thr Ser Thr Thr Thr
485                 490                 495                 500

TCG AAG AAT CGC ATC ATC ATA ACC TGG CAC CGG TAC CGG CCC CCT GAC      1593
Ser Lys Asn Arg Ile Ile Ile Thr Trp His Arg Tyr Arg Pro Pro Asp
                505                 510                 515

TAC AGG GAT CTC ATC AGC TTC ACC GTT TAC TAC AAG GAA GCA CCC TTT      1641
Tyr Arg Asp Leu Ile Ser Phe Thr Val Tyr Tyr Lys Glu Ala Pro Phe
        520                 525                 530
```

```
AAG AAT GTC ACA GAG TAT GAT GGG CAG GAT GCC TGC GGC TCC AAC AGC    1689
Lys Asn Val Thr Glu Tyr Asp Gly Gln Asp Ala Cys Gly Ser Asn Ser
        535                 540                 545

TGG AAC ATG GTG GAC GTG GAC CTC CCG CCC AAC AAG GAC GTG GAG CCC    1737
Trp Asn Met Val Asp Val Asp Leu Pro Pro Asn Lys Asp Val Glu Pro
550                 555                 560

GGC ATC TTA CTA CAT GGG CTG AAG CCC TGG ACT CAG TAC GCC GTT TAC    1785
Gly Ile Leu Leu His Gly Leu Lys Pro Trp Thr Gln Tyr Ala Val Tyr
565                 570                 575                 580

GTC AAG GCT GTG ACC CTC ACC ATG GTG GAG AAC GAC CAT ATC CGT GGG    1833
Val Lys Ala Val Thr Leu Thr Met Val Glu Asn Asp His Ile Arg Gly
                585                 590                 595

GCC AAG AGT GAG ATC TTG TAC ATT CGC ACC AAT GCT TCA GTT CCT TCC    1881
Ala Lys Ser Glu Ile Leu Tyr Ile Arg Thr Asn Ala Ser Val Pro Ser
        600                 605                 610

ATT CCC TTG GAC GTT CTT TCA GCA TCG AAC TCC TCT TCT CAG TTA ATC    1929
Ile Pro Leu Asp Val Leu Ser Ala Ser Asn Ser Ser Ser Gln Leu Ile
            615                 620                 625

GTG AAG TGG AAC CCT CCC TCT CTG CCC AAC GGC AAC CTG AGT TAC TAC    1977
Val Lys Trp Asn Pro Pro Ser Leu Pro Asn Gly Asn Leu Ser Tyr Tyr
630                 635                 640

ATT GTG CGC TGG CAG CGG CAG CCT CAG GAC GGC TAC CTT TAC CGG CAC    2025
Ile Val Arg Trp Gln Arg Gln Pro Gln Asp Gly Tyr Leu Tyr Arg His
645                 650                 655                 660

AAT TAC TGC TCC AAA GAC AAA ATC CCC ATC AGG AAG TAT GCC GAC GGC    2073
Asn Tyr Cys Ser Lys Asp Lys Ile Pro Ile Arg Lys Tyr Ala Asp Gly
                665                 670                 675

ACC ATC GAC ATT GAG GAG GTC ACA GAG AAC CCC AAG ACT GAG GTG TGT    2121
Thr Ile Asp Ile Glu Glu Val Thr Glu Asn Pro Lys Thr Glu Val Cys
            680                 685                 690

GGT GGG GAG AAA GGG CCT TGC TGC GCC TGC CCC AAA ACT GAA GCC GAG    2169
Gly Gly Glu Lys Gly Pro Cys Cys Ala Cys Pro Lys Thr Glu Ala Glu
        695                 700                 705

AAG CAG GCC GAG AAG GAG GAG GCT GAA TAC CGC AAA GTC TTT GAG AAT    2217
Lys Gln Ala Glu Lys Glu Glu Ala Glu Tyr Arg Lys Val Phe Glu Asn
    710                 715                 720

TTC CTG CAC AAC TCC ATC TTC GTG CCC AGA CCT GAA AGG AAG CGG AGA    2265
Phe Leu His Asn Ser Ile Phe Val Pro Arg Pro Glu Arg Lys Arg Arg
725                 730                 735                 740

GAT GTC ATG CAA GTG GCC AAC ACC ACC ATG TCC AGC CGA AGC AGG AAC    2313
Asp Val Met Gln Val Ala Asn Thr Thr Met Ser Ser Arg Ser Arg Asn
                745                 750                 755

ACC ACG GCC GCA GAC ACC TAC AAC ATC ACC GAC CCG GAA GAG CTG GAG    2361
Thr Thr Ala Ala Asp Thr Tyr Asn Ile Thr Asp Pro Glu Glu Leu Glu
            760                 765                 770

ACA GAG TAC CCT TTC TTT GAG AGC AGA GTG GAT AAC ACG GAG AGA ACT    2409
Thr Glu Tyr Pro Phe Phe Glu Ser Arg Val Asp Asn Thr Glu Arg Thr
        775                 780                 785

GTC ATT TCT AAC CTT CGG CCT TTC ACA TTG TAC CGC ATC GAT ATC CAC    2457
Val Ile Ser Asn Leu Arg Pro Phe Thr Leu Tyr Arg Ile Asp Ile His
    790                 795                 800

AGC TGC AAC CAC GAG GCT GAG AAG CTG GGC TGC AGC GCC TCC AAC TTC    2505
Ser Cys Asn His Glu Ala Glu Lys Leu Gly Cys Ser Ala Ser Asn Phe
805                 810                 815                 820

GTC TTT GCA AGG ACT ATG CCC GCA GAA GGA GCA GAT GAC ATT CCT GGG    2553
Val Phe Ala Arg Thr Met Pro Ala Glu Gly Ala Asp Asp Ile Pro Gly
                825                 830                 835

CCA GTG ACC TGG GAG CCA AGG CCT GAA AAC TCC ATC TTT TTA AAG TGG    2601
Pro Val Thr Trp Glu Pro Arg Pro Glu Asn Ser Ile Phe Leu Lys Trp
```

-continued

```
              840                    845                        850
CCG GAA CCT GAG AAT CCC AAT GGA TTG ATT CTA ATG TAT GAA ATA AAA        2649
Pro Glu Pro Glu Asn Pro Asn Gly Leu Ile Leu Met Tyr Glu Ile Lys
            855                    860                    865

TAC GGA TCA CAA GTT GAG GAT CAG CGA GAA TGT GTG TCC AGA CAG GAA        2697
Tyr Gly Ser Gln Val Glu Asp Gln Arg Glu Cys Val Ser Arg Gln Glu
    870                    875                    880

TAC AGG AAG TAT GGA GGG GCC AAG CTA AAC CGG CTA AAC CCG GGG AAC        2745
Tyr Arg Lys Tyr Gly Gly Ala Lys Leu Asn Arg Leu Asn Pro Gly Asn
885                    890                    895                    900

TAC ACA GCC CGG ATT CAG GCC ACA TCT CTC TCT GGG AAT GGG TCG TGG        2793
Tyr Thr Ala Arg Ile Gln Ala Thr Ser Leu Ser Gly Asn Gly Ser Trp
            905                    910                    915

ACA GAT CCT GTG TTC TTC TAT GTC CAG GCC AAA ACA GGA TAT GAA AAC        2841
Thr Asp Pro Val Phe Phe Tyr Val Gln Ala Lys Thr Gly Tyr Glu Asn
            920                    925                    930

TTC ATC CAT CTG ATC ATC GCT CTG CCC GTC GCT GTC CTG TTG ATC GTG        2889
Phe Ile His Leu Ile Ile Ala Leu Pro Val Ala Val Leu Leu Ile Val
            935                    940                    945

GGA GGG TTG GTG ATT ATG CTG TAC GTC TTC CAT AGA AAG AGA AAT AAC        2937
Gly Gly Leu Val Ile Met Leu Tyr Val Phe His Arg Lys Arg Asn Asn
        950                    955                    960

AGC AGG CTG GGG AAT GGA GTG CTG TAT GCC TCT GTG AAC CCG GAG TAC        2985
Ser Arg Leu Gly Asn Gly Val Leu Tyr Ala Ser Val Asn Pro Glu Tyr
965                    970                    975                    980

TTC AGC GCT GCT GAT GTG TAC GTT CCT GAT GAG TGG GAG GTG GCT CGG        3033
Phe Ser Ala Ala Asp Val Tyr Val Pro Asp Glu Trp Glu Val Ala Arg
                985                    990                    995

GAG AAG ATC ACC ATG AGC CGG GAA CTT GGG CAG GGG TCG TTT GGG ATG        3081
Glu Lys Ile Thr Met Ser Arg Glu Leu Gly Gln Gly Ser Phe Gly Met
                1000                    1005                    1010

GTC TAT GAA GGA GTT GCC AAG GGT GTG GTG AAA GAT GAA CCT GAA ACC        3129
Val Tyr Glu Gly Val Ala Lys Gly Val Val Lys Asp Glu Pro Glu Thr
            1015                    1020                    1025

AGA GTG GCC ATT AAA ACA GTG AAC GAG GCC GCA AGC ATG CGT GAG AGG        3177
Arg Val Ala Ile Lys Thr Val Asn Glu Ala Ala Ser Met Arg Glu Arg
        1030                    1035                    1040

ATT GAG TTT CTC AAC GAA GCT TCT GTG ATG AAG GAG TTC AAT TGT CAC        3225
Ile Glu Phe Leu Asn Glu Ala Ser Val Met Lys Glu Phe Asn Cys His
1045                    1050                    1055                    1060

CAT GTG GTG CGA TTG CTG GGT GTG GTG TCC CAA GGC CAG CCA ACA CTG        3273
His Val Val Arg Leu Leu Gly Val Val Ser Gln Gly Gln Pro Thr Leu
                1065                    1070                    1075

GTC ATC ATG GAA CTG ATG ACA CGG GGC GAT CTC AAA AGT TAT CTC CGG        3321
Val Ile Met Glu Leu Met Thr Arg Gly Asp Leu Lys Ser Tyr Leu Arg
            1080                    1085                    1090

TCT CTG AGG CCA GAA ATG GAG AAT AAT CCA GTC CTA GCA CCT CCA AGC        3369
Ser Leu Arg Pro Glu Met Glu Asn Asn Pro Val Leu Ala Pro Pro Ser
        1095                    1100                    1105

CTG AGC AAG ATG ATT CAG ATG GCC GGA GAG ATT GCA GAC GGC ATG GCA        3417
Leu Ser Lys Met Ile Gln Met Ala Gly Glu Ile Ala Asp Gly Met Ala
            1110                    1115                    1120

TAC CTC AAC GCC AAT AAG TTC GTC CAC AGA GAC CTT GCT GCC CGG AAT        3465
Tyr Leu Asn Ala Asn Lys Phe Val His Arg Asp Leu Ala Ala Arg Asn
1125                    1130                    1135                    1140

TGC ATG GTA GCC GAA GAT TTC ACA GTC AAA ATC GGA GAT TTT GGT ATG        3513
Cys Met Val Ala Glu Asp Phe Thr Val Lys Ile Gly Asp Phe Gly Met
                1145                    1150                    1155

ACG CGA GAT ATC TAT GAG ACA GAC TAT TAC CGG AAA GGA GGC AAA GGG        3561
```

-continued

```
Thr Arg Asp Ile Tyr Glu Thr Asp Tyr Tyr Arg Lys Gly Gly Lys Gly
        1160                1165                1170

CTG CTG CCC GTG CGC TGG ATG TCT CCT GAG TCC CTC AAG GAT GGA GTC      3609
Leu Leu Pro Val Arg Trp Met Ser Pro Glu Ser Leu Lys Asp Gly Val
        1175                1180                1185

TTC ACC ACT TAC TCG GAC GTC TGG TCC TTC GGG GTC GTC CTC TGG GAG      3657
Phe Thr Thr Tyr Ser Asp Val Trp Ser Phe Gly Val Val Leu Trp Glu
        1190                1195                1200

ATC GCC ACA CTG GCC GAG CAG CCC TAC CAG GGC TTG TCC AAC GAG CAA      3705
Ile Ala Thr Leu Ala Glu Gln Pro Tyr Gln Gly Leu Ser Asn Glu Gln
1205                1210                1215                1220

GTC CTT CGC TTC GTC ATG GAG GGC GGC CTT CTG GAC AAG CCA GAC AAC      3753
Val Leu Arg Phe Val Met Glu Gly Gly Leu Leu Asp Lys Pro Asp Asn
        1225                1230                1235

TGT CCT GAC ATG CTG TTT GAA CTG ATG CGC ATG TGC TGG CAG TAT AAC      3801
Cys Pro Asp Met Leu Phe Glu Leu Met Arg Met Cys Trp Gln Tyr Asn
        1240                1245                1250

CCC AAG ATG AGG CCT TCC TTC CTG GAG ATC ATC AGC AGC ATC AAA GAG      3849
Pro Lys Met Arg Pro Ser Phe Leu Glu Ile Ile Ser Ser Ile Lys Glu
        1255                1260                1265

GAG ATG GAG CCT GGC TTC CGG GAG GTC TCC TTC TAC TAC AGC GAG GAG      3897
Glu Met Glu Pro Gly Phe Arg Glu Val Ser Phe Tyr Tyr Ser Glu Glu
        1270                1275                1280

AAC AAG CTG CCC GAG CCG GAG GAG CTG GAC CTG GAG CCA GAG AAC ATG      3945
Asn Lys Leu Pro Glu Pro Glu Glu Leu Asp Leu Glu Pro Glu Asn Met
1285                1290                1295                1300

GAG AGC GTC CCC CTG GAC CCC TCG GCC TCC TCG TCC TCC CTG CCA CTG      3993
Glu Ser Val Pro Leu Asp Pro Ser Ala Ser Ser Ser Ser Leu Pro Leu
        1305                1310                1315

CCC GAC AGA CAC TCA GGA CAC AAG GCC GAG AAC GGC CCC GGC CCT GGG      4041
Pro Asp Arg His Ser Gly His Lys Ala Glu Asn Gly Pro Gly Pro Gly
        1320                1325                1330

GTG CTG GTC CTC CGC GCC AGC TTC GAC GAG AGA CAG CCT TAC GCC CAC      4089
Val Leu Val Leu Arg Ala Ser Phe Asp Glu Arg Gln Pro Tyr Ala His
        1335                1340                1345

ATG AAC GGG GGC CGC AAG AAC GAG CGG GCC TTG CCG CTG CCC CAG TCT      4137
Met Asn Gly Gly Arg Lys Asn Glu Arg Ala Leu Pro Leu Pro Gln Ser
        1350                1355                1360

TCG ACC TGC TGA TCCTTGGATC CTGAATCTGT GCAAACAGTA ACGTGTGCGC ACGCGC   4195
Ser Thr Cys
1365

AGCGGGGTGG GGGGGGAGAG AGAGTTTTAA CAATCCATTC ACAAGCCTCC TGTACCTCAG   4255

TGGATCTTCA GTTCTGCCCT TGCTGCCCGC GGGAGACAGC TTCTCTGCAG TAAAACACAT   4315

TTGGGATGTT CCTTTTTTCA ATATGCAAGC AGCTTTTTAT TCCCTGCCCA AACCCTTAAC   4375

TGACATGGGC CTTTAAGAAC CTTAATGACA ACACTTAATA GCAACAGAGC ACTTGAGAAC   4435

CAGTCTCCTC ACTCTGTCCC TGTCCTTCCC TGTTCTCCCT TTCTCTCTCC TCTCTGCTTC   4495

ATAACGGAAA AATAATTGCC ACAAGTCCAG CTGGGAAGCC CTTTTTATCA GTTTGAGGAA   4555

GTGGCTGTCC CTGTGGCCCC ATCCAACCAC TGTACACACC CGCCTGACAC CGTGGGTCAT   4615

TACAAAAAAA CACGTGGAGA TGGAAATTTT TACCTTTATC TTTCACCTTT CTAGGGACAT   4675

GAAATTTACA AAGGGCCATC GTTCATCCAA GGCTGTTACC ATTTTAACGC TGCCTAATTT   4735

TGCCAAAATC CTGAACTTTC TCCCTCATCG GCCCGGCGCT GATTCCTCGT GTCCGGAGGC   4795

ATGGGTGAGC ATGGCAGCTG GTTGCTCCAT TTGAGAGACA CGCTGGCGAC ACACTCCGTC   4855

CATCCGACTG CCCCTGCTGT GCTGCTCAAG GCCACAGGCA CACAGGTCTC ATTGCTTCTG   4915
```

```
                                                                  -continued
ACTAGATTAT TATTTGGGGG AACTGGACAC AATAGGTCTT TCTCTCAGTG AAGGTGGGGA    4975

GAAGCTGAAC CGGC                                                     4989
```